US009352323B2

(12) United States Patent
Duerr et al.

(10) Patent No.: US 9,352,323 B2
(45) Date of Patent: May 31, 2016

(54) LABORATORY APPARATUS AND METHOD FOR HANDLING LABORATORY SAMPLES

(75) Inventors: Florian Duerr, Hamburg (DE); Ruediger Huhn, Luebeck (DE); Manuel Mayer, Bad Oldesloe (DE); Janine Roehrs, Hamburg (DE); Gerrit Walter, Hamburg (DE); Wolf Wente, Hamburg (DE)

(73) Assignee: EPPENDORF AF, Hamburg (DE)

( * ) Notice: Subject to any disclaimer, the term of this patent is extended or adjusted under 35 U.S.C. 154(b) by 95 days.

(21) Appl. No.: 13/565,705

(22) Filed: Aug. 2, 2012

(65) Prior Publication Data

US 2013/0045473 A1 Feb. 21, 2013

Related U.S. Application Data

(60) Provisional application No. 61/514,525, filed on Aug. 3, 2011.

(30) Foreign Application Priority Data

Aug. 3, 2011 (DE) ........................ 10 2011 109 332

(51) Int. Cl.

*C12M 1/34* (2006.01)
*B01L 9/00* (2006.01)
*B01F 11/00* (2006.01)
*B01F 15/00* (2006.01)

(52) U.S. Cl.

CPC ............. *B01L 9/523* (2013.01); *B01F 11/0014* (2013.01); *B01F 15/00155* (2013.01); *B01F 15/00253* (2013.01); *B01F 2215/0037* (2013.01); *B01L 2200/023* (2013.01); *B01L 2200/143* (2013.01); *Y10T 436/12* (2015.01)

(58) Field of Classification Search

None
See application file for complete search history.

(56) References Cited

U.S. PATENT DOCUMENTS 5,250,801 A * 10/1993 Grozinger et al. ........ 250/223 B
5,779,907 A 7/1998 Yu (Continued)

FOREIGN PATENT DOCUMENTS

DE 20017342 U1 2/2001
DE 10 2010 019 232 A1 * 1/2006

(Continued)

*Primary Examiner* — Chris L Chin
(74) *Attorney, Agent, or Firm* — Todd A. Lorenz; Arnold & Porter LLP

(57) ABSTRACT

The invention relates to a laboratory apparatus for handling at least one laboratory sample, in particular for mixing and/or adjusting the temperature of a biochemical laboratory sample, which is arranged in at least one sample vessel element, having a carrier device for carrying the at least one sample vessel element, an electrical control device, which is set up for controlling or setting at least one operating parameter of the laboratory apparatus that controls this handling, and at least one sensor device for recording at least one measured value, by which at least one geometrical property of the at least one sample vessel element can be determined, the at least one sensor device being signal-connected to the electrical control device, the electrical control device being set up for controlling the handling of the at least one laboratory sample in dependence on the at least one measured value and the at least one set operating parameter by at least one control step. The invention also relates to a method for handling at least one laboratory sample by means of a laboratory apparatus and to a computer program product for performing the method.

13 Claims, 11 Drawing Sheets

(56) References Cited

U.S. PATENT DOCUMENTS

| | | | |
|---|---|---|---|
| 5,904,421 | A | 5/1999 | Mazzalveri |
| 6,143,578 | A | 11/2000 | Bendele et al. |
| 6,210,958 | B1 * | 4/2001 | Brust et al. ................. 435/287.2 |
| 6,605,213 | B1 | 8/2003 | Ammann et al. |
| 6,767,512 | B1 * | 7/2004 | Lurz et al. ..................... 422/552 |
| 6,884,357 | B2 | 4/2005 | Siddiqi |
| 6,891,182 | B2 * | 5/2005 | Watari et al. ............. 250/559.19 |
| D569,988 | S * | 5/2008 | Koop ........................... D24/220 |
| 7,628,064 | B1 * | 12/2009 | Miller et al. .................... 73/149 |
| 7,954,406 | B2 | 6/2011 | Tanki et al. |
| 7,985,375 | B2 | 7/2011 | Edens et al. |
| 2001/0035492 | A1 * | 11/2001 | Estevez-Garcia ............. 250/221 |
| 2003/0012699 | A1 | 1/2003 | Moore et al. |
| 2004/0029772 | A1 | 2/2004 | Konietzko |
| 2004/0151064 | A1 | 8/2004 | Yi |
| 2006/0153736 | A1 | 7/2006 | Kalra et al. |
| 2006/0187743 | A1 | 8/2006 | Carreras |
| 2007/0132723 | A1 * | 6/2007 | Lurz et al. ..................... 345/156 |
| 2007/0211566 | A1 | 9/2007 | Ebers et al. |
| 2007/0280036 | A1 | 12/2007 | Carreras |
| 2008/0056059 | A1 | 3/2008 | Manera et al. |
| 2009/0082214 | A1 | 3/2009 | Liu et al. |
| 2009/0130679 | A1 | 5/2009 | Wu et al. |
| 2009/0133971 | A1 * | 5/2009 | Baier-Welt ............... 188/1.11 E |
| 2009/0134069 | A1 | 5/2009 | Handique |
| 2010/0167406 | A1 | 7/2010 | Streit et al. |
| 2010/0303690 | A1 | 12/2010 | Howell et al. |
| 2011/0003380 | A1 | 1/2011 | Miltenyi et al. |
| 2011/0031420 | A1 * | 2/2011 | Gotz et al. .................... 250/577 |
| 2011/0287447 | A1 | 11/2011 | Norderhaug et al. |

FOREIGN PATENT DOCUMENTS

| | | | |
|---|---|---|---|
| DE | 102006011370 | A1 | 9/2007 |
| DE | 102008047623 | A1 | 4/2010 |
| DE | 102010019232 | A1 | 11/2011 |
| GB | 2451491 | A | 2/2009 |
| WO | WO 01/05510 | A1 | 1/2001 |
| WO | WO 03/090897 | A1 | 11/2003 |
| WO | WO 2010/037862 | A1 | 4/2010 |
| WO | WO 2011/138003 | A1 | 11/2011 |

* cited by examiner

LABORATORY APPARATUS AND METHOD FOR HANDLING LABORATORY SAMPLES

The invention relates to a laboratory apparatus for handling laboratory samples, in particular a laboratory apparatus for mixing and/or adjusting the temperature of a liquid sample in a medical, biological or biochemical laboratory. The invention also relates to a method for handling such laboratory samples.

Laboratory samples in medical, biological or biochemical laboratories contain elements with molecular or cellular dimensions, for example biochemical analytes and reagents, bacteria or cells. The functionality of the samples to be treated is usually crucially dependent on external ambient parameters (temperature, pH, etc.), which have to be adapted to specific conditions, particularly, where required the living conditions of the elements contained. Due to the sensitivity of such samples, there are special requirements for their handling and processing with regard to care and precision. The laboratory samples are typically processed in extremely small sample volumes ranging between a few microliters and milliliters. The usually tubular sample vessels used for sample handling are arranged in the corresponding laboratory apparatus and then (semi) automatically handled/processed, for example they are subjected to a temperature-adjusting process and/or a mixing process.

The nature of the used sample vessel has a direct influence on the efficiency of the handling in the laboratory apparatus. For example, the dimensioning, material and wall thickness of sample vessels are of significance if samples are to be heated and cooled according to a temperature-adjusting program.

In laboratory apparatuses where the feasibility or efficiency of the heat transfer depends on the geometry of the sample vessel, various error situations can occur. For example, in the case of temperature-adjusting devices with heatable condensation avoidance hoods (such as disclosed in DE 10 2010 019 232) under which sample vessels of excessive heights are placed, overheating of the sample vessels can occur. In this case, laboratory samples may be damaged or destroyed. Since such laboratory samples sometimes represent a considerable material value or are attributed special importance, for example in the case of forensic laboratory samples, the user has to handle the laboratory apparatuses processing such samples with extreme care.

A further example is a laboratory apparatus for mixing samples. The result of a mixing process is influenced by the mass and the centre of gravity of a sample vessel element and the operating mode that is used. With known laboratory sample mixing devices it was for example observed that sample vessels can cause great imbalances or where even thrown from their mounting, causing sample loss, if the sample vessels carried an excessive mass or the oscillating mixing movement was conducted with excessive frequencies and amplitude DE 10 2006 011 370 has therefore proposed an improved laboratory sample mixing device in which an acceleration sensor indirectly carries out a mass determination and/or a mass-dependent vibration analysis and, if required, reduces the rotational speed. However, certain errors cannot be excluded in this way. Particularly for dynamic measurements, the movement of the sample vessel must have already commenced to allow determination of a result, thus errors may already occur before adaptation of the rotational speed. Furthermore, this concept is not suitable for those laboratory apparatuses in which the laboratory samples are not moved.

It is an object of the present invention to provide a laboratory apparatus and a method for handling at least one laboratory sample with which the reliability of the handling of the laboratory sample is improved.

The invention achieves this object with the laboratory apparatus for handling at least one laboratory sample according to Claim 1 and the method for handling at least one laboratory sample according to Claim 16 and the computer program product with a computer program according to Claim 18. Preferred configurations of the invention are the subject of the subclaims.

In a first preferred embodiment of the invention, the laboratory apparatus is designed as a laboratory mixing device. In a second preferred embodiment of the invention, the laboratory apparatus is designed as a laboratory temperature-adjusting device. In a third preferred embodiment of the invention, the laboratory apparatus is designed as a combined laboratory mixing device and laboratory temperature-adjusting device. Further functions and ways of handling laboratory samples of the laboratory apparatus are also possible in each case. However, the invention is not restricted to these embodiments. Preferred properties and advantages of the laboratory apparatus according to the invention and of the method according to the invention for handling laboratory samples are further described below.

The invention offers the advantage that starting of the handling, in particular after the obtainment of a starting signal for starting the handling of a laboratory sample according to the at least one operating parameter, the starting does not take place unconditionally but includes at least one control step, whereby the starting depends on the at least one measured value of the at least one geometrical property of the at least one sample vessel element. As a consequence, the handling of the at least one laboratory sample is more safe and dependable.

For this purpose, the control device preferably performs before the actual starting of the handling a control step, i.e. before starting of the movement or before changing of a mixing movement in the case of a laboratory mixing device or before starting of the temperature adjustment or before changing of the temperature adjustment in the case of a laboratory temperature-adjusting device. By means of this control step, it can be automatically checked whether a planned setting or changing of the operating parameter is compatible with the detected measured value, representing a geometrical property of the sample vessel element. Depending on the measured value, a predetermined operating parameter for the handling may not be changed and authorized for handling, or may be changed, or an enquiry may be directed to the user or the handling may be interrupted or terminated. The starting signal preferably takes place by a user input being carried out by means of a user interface of the laboratory apparatus. This user input may take place before the beginning of a handling, after an operating parameter has been chosen, for example manually, or may take place during the handling, if for example the user manually changes the current operating parameter.

The geometrical property may be a dimension of the at least one sample vessel element, for example a height value, a width value or a depth value, in particular the maximum or characteristic height, width or depth of a sample vessel element. A geometrical property may be, for example, the logical result value of a geometric comparison, for example the comparison of the measured value with a reference value, i.e. determining whether the measured value is greater or smaller than a reference value. The result value may also be the difference or the ratio of the measured value and the reference value. The reference value may, for example, be the known position of a sensor element with reference to the position of the support point of the sample vessel element or of the receiving region of the carrier plate for the sample vessel element. The exemplary embodiment shown in FIGS. 4*a*, 4*b*, explain how a height measuring device for carrying out a geometrical comparison can be realized with an optical sensor device in order to obtain a result value that represents the geometrical property of the sample vessel element.

By taking into account the at least one geometrical property of the at least one sample vessel element, it is in particularly achievable to handle the laboratory samples in the sample vessel elements according to their geometrical properties. By taking a measurement, the at least one geometrical property of the sample vessel element is determinable and can be taken into consideration or determined in particular by one or more control steps of the control device. This allows certain errors to be prevented, in particular those which would not be detectable when only measuring the mass of the sample vessel elements.

For example, it can be prevented that the handling carried out is not compatible with a certain height of a sample vessel element. This has the advantage that the risk of developing an imbalance is reduced and thus the stability of the device is increased. This produces the overall advantage of a general increase in safety. For example in the case of the oscillating mixing movement of a laboratory mixing device it is possible to prevent the samples from being thrown off or damaged, which can occur if at the chosen rotational speed, the holding forces would be overcome due to the geometrical centre of gravity of the sample vessel element. Furthermore, for example in the case of a laboratory temperature-adjusting device, it can happen that the setpoint temperature of a condensation avoidance hood arranged over the sample vessel element is set too high and the sample is thus thermally damaged.

In a preferred embodiment of the invention, the electrical control device is set up for conducting at least one control step after the obtainment of a starting signal for starting the handling according to the at least one operating parameter, the at least one operating parameter being able to be changed, if required, by this control step in dependence on the at least one measured value recorded (determined measured value) and the handling either being carried out or not carried out, in particular the handling either being interrupted or terminated, by the control step.

The control device controls/operates the handling in dependence on the measured value. A control mode e.g. can include carrying out a predetermined first handling, if the measured value fulfils a first condition, e.g. lies within a predetermined first range of values, and further, carrying out a second predetermined handling, if the measured value fulfils a second condition, e.g.

lies within a predetermined second range of values, wherein said ranges can be saved in a memory of the laboratory apparatus. There can be more than two conditions and associated handlings, for achieving a higher differentiated control.

In case that the control of the control system is configured to perform a yes/no-decision in dependence on a measured value, using a single condition, there can be a first handling, which is performed if the condition is fulfilled and a second handling if the condition is not fulfilled. The first handling can be, as described, that no handling is carried out at all (no action taken) and the alternative handling can be to carry out one predetermined handling, e.g. setting of a control parameter of the laboratory apparatus.

One advantage of the invention according to said embodiments is, in particular, that changes of the sample vessel that occur in the time period between the loading of the laboratory apparatus with the sample vessel element and the start of the handling, in particular directly before the start of the handling, are taken into consideration by the control step, since the consideration of the measured value takes place in the same control step that also performs the handling, in order for example to modify, interrupt or terminate it if required. By carrying out this check directly before the handling of the laboratory sample, a reliable and correct setting of the operating parameter is ensured, or, if required, a termination or interruption of the handling is possible, in order for example to direct a further safety enquiry to the user.

Preferred configurations of the invention make it possible furthermore to exclude certain errors which in the case of laboratory apparatuses could lead to undesired impairments of the handling result due to unsuitable handling of samples contained in typical sample vessel elements (for example standard sample vessels). For example, in the case of a laboratory mixing device it is possible to exclude the possibility of a type of sample vessel element with, for example, an unsuitably great height being automatically handled with an excessive oscillation frequency or amplitude after starting, which could lead to the sample vessel element being thrown off from the laboratory mixing device. Furthermore, for example, the escape of sample material from the sample vessels, particularly spilling, and generally the loss of sample, can be prevented.

The samples that can be moved by the laboratory mixing device are preferably fluid, in particular liquid, for example aqueous, but may also be powdered, granular, pasty or mixtures thereof. They are preferably laboratory samples or solutions which are examined and/or processed in chemical, biochemical, biological, medical, life-science or forensic laboratories.

The sample vessel element may be a single vessel element, for example a sample tube, or a multiple vessel element, for example a microtitre plate or PCR plate, or a series, grid or network of interconnected sample vessels. Typical sample volumes are in the range of a few μl to several tens or hundreds of μl, or one or more milliliters up to 100 ml. Multiple vessel elements are often configured as vessel arrays arranged in the manner of a grid, which extend downwards from an upper horizontal connecting level in which neighbouring vessels are connected by connecting portions. The lower region of the vessels is usually surrounded by a contiguous hollow space, or a number of hollow spaces, in which there can engage, for example, one or more vessel receiving devices, which may for example be part of a vessel holder part or a temperature-adjusting block.

A sample vessel element may have a covering device, cover device or sealing device, which in each case closes the upwardly facing opening of a vessel (or a number of or all of the openings) of the sample vessel element. Known are, for example, individual caps, cap strips, cap arrays, sealing foils or a cover for a number of or all of the vessels of a multiple vessel element.

Sample vessel elements, in particular multiple vessel elements, for example microtitre plates, preferably have a frame portion, which frames the horizontally external sides of the sample vessel element. Such a frame then defines the lateral outer dimensions of the sample vessel element, in particular also the lateral dimensions of a receiving region. The carrier device is preferably configured in such a way that the sensor device is arranged laterally alongside the frame portion when a sample vessel element is arranged on the carrier device. The frame portion is particularly suitable as a target region for the sensor device and preferably has an interacting portion for interaction with the sensor device.

Various types of sample vessel elements, in particular multiple vessel elements, are known or can be defined. Actual examples of types of sample vessel elements are cryo vessels, Falcon vessels (1.5 ml and 50 ml), glass vessels and beakers, microtitre plates (MTP), deep-well plates (DWP), slides and PCR plates with 96 or 384 wells. In comparison with "normal" microtitre plates, DWPs have a greater plate and vessel height and have a greater mass. According to the ANSI standard and the recommendation of the Society of Biomolecular Screening (SBS), the dimensions (length×width×height) of microtitre plates are 127.76 mm×85.48 mm×14.35 mm. Relevant standards for these standardized dimensions are, for example, ANSI/SBS 1-2004, ANSI/SBS 2-2004, ANSI/SBS 3-2004 and ANSI/SBS 4-2004. A sample vessel element defined by one of these standards or some other standard is referred to in the present case as a standard type. Such a type or a standard type may refer to sample vessel elements that are constructed in the same way or may refer to groups of sample vessel elements that are the same in at least one typical or standardized property, for example height.

Different types of sample vessel elements are preferably distinguishable by at least one typical property. This typical property is used to determine the measured value that is representative of the at least one geometrical property of the sample vessel element. The height of the sample vessel element, which can be measured by means of a sensor device designed as a height measuring device, is preferably used as this property or as the representative measured value.

The typical property may, however, also be differently measured, for example by the measuring of a geometrical extent of the sample vessel element, for example a width, depth or height, preferably a typical or maximum width, depth or height. The typical property may also be a physical property of the sample vessel element, for example the ability to reflect a transmitted measuring signal, the ability to modify a transmitted measuring signal, for example a radio-frequency signal in the case of RFID sensors and chips, or some other property by which the type of sample vessel element can be represented.

The property may also be contained in coded form in a coding device which is arranged on the sample vessel element and is read by the sensor device in order to read the code of the sample vessel element, which identifies either the type of sample vessel element or even, preferably additionally, the individual sample vessel element. Using an assignment table, which may be stored in the control device, the type and/or the individual sample vessel element is then inferred on the basis of the code.

The determined type or standard type of a sample vessel element is representative of the geometrical property of the sample vessel element. The at least one geometrical property of the sample vessel element is preferably inferred or taken into consideration before the handling of the sample(s) starts.

The measured value is preferably representative of the type, particularly a standard type, of the at least one sample vessel element, the control device preferably being designed for carrying out a comparative operation, in which the measured value is compared with previously known sample vessel type data and the type is detected, and for carrying out at least one of these further control steps in dependence on the result of this comparison.

The control device preferably has means for carrying out the control step or a number of control steps, in particular of a method of checking. These means may include means for evaluating the at least one measured value and means for carrying out a comparative operation. Means of the control device that are set up for carrying out the type detection of a sample vessel element, or possibly the individual detection of a sample vessel element, are also referred to as an identification device. Means for carrying out the control step may in each case be designed, for example, as electrical circuits and/or as programmable electrical circuits and or as a computer program product with a computer program for carrying out the method of checking or method of identification.

Sample vessel type data are data which contain, and in particular encode, the information concerning at least one type or standard type of sample vessel elements. There are preferably at least two sample vessel type data, in order to be able preferably to distinguish between at least two sample vessel types, preferably a multiplicity of sample vessel types. The sample vessel type data may be contained in an assignment table, which may be stored in the control device or which is accessed by the control device by way of a signal link to a storage device that is external with respect to the laboratory apparatus.

The fact that the type or standard type of the sample vessel element is detected means that there is a greater error tolerance with respect to the recording of the measuring device by means of the sensor device. Unlike in the case of known laboratory apparatuses, a property, for example a mass or a vibration analysis, does not have to be determined or carried out precisely, but instead a measured value only has to be determined sufficiently accurately to detect the presence of a specific sample vessel element or type of sample vessel element. As a consequence, the measurement is simpler and the expenditure for providing the sensor device is less. Detecting the type or standard type of the sample vessel element makes this at least one geometrical property of the sample vessel element determinable and able to be taken into consideration or determined in particular by one or more control steps of the control device.

Furthermore, it is preferably provided that this measured value represents an individual sample vessel element, the control device being designed for using this measured value to distinguish the individual sample vessel element from a multiplicity of other individual sample vessel elements. In this way, the presence of an individual sample vessel element on the laboratory apparatus can be detected. The geometrical properties of this sample vessel element can be determined by way of this individual measured value, for example by means of an assignment table, which can be used to infer the geometrical property unequivocally. Depending on this individual measured value, further handling steps may likewise be chosen individually, either automatically by the control device and/or by the user. The detection or distinguishing of the individual sample vessel element may take place by way of a coding device, by means of decoding and comparison by the control device, or in other ways.

The measured value with the information for identifying the individual sample vessel element preferably also contains information concerning the type of sample vessel element. The control device is then preferably designed for both obtaining the information for identifying the individual sample vessel element and preferably also obtaining the information concerning the type of sample vessel element and, if required, for carrying out further control steps in dependence on these items of information.

The control step is preferably part of a method for handling the at least one laboratory sample that is performed by starting the handling by the control device, in particular computer-program-aided, in particular by means of a handling program.

In the method for handling, and in particular in the control step in which the measured value is taken into consideration, the measured value is preferably determined during a measuring process of the sensor device, preferably after the obtainment of a starting signal for starting the handling and before the actual starting of the handling. Preferably, the actual handling of the laboratory sample, that is to say for example the temperature adjustment and/or moving of a laboratory sample, is started automatically in this control step. As a consequence, the checking of the compatibility of the sample vessel element with the predetermined operating parameter is adapted directly before the handling, whereby safe and dependable handling is achieved.

The predetermined operating parameter, which was either manually chosen by a user or automatically provided by a predetermined procedure of the laboratory apparatus, in particular a computer program of the laboratory apparatus, is taken into account during the performance of the control step(s) (in short "check-up"), and depending on the results of the check-up, is either adapted or used unmodified to operate the laboratory apparatus. The computer program may be provided in the laboratory apparatus, in particular it can be stored/saved in an unchangeable form or in a form manipulable by the manufacturer or the user.

The starting signal for starting the handling is preferably the starting signal for starting the method for handling, in particular a handling program, which particularly comprises this control step. This handling program may be stored/saved in the laboratory apparatus and may be in a form in which it can be manipulated by the user. Starting the handling may mean in particular starting the mixing of the at least one laboratory sample or the temperature adjustment of the at least one sample vessel element.

The further control steps that are carried out by the control device in dependence on this measured value may comprise the following steps: preferably the control step allows that starting the setting of the at least one operating parameter is either continued, delayed, interrupted or is terminated, respectively. The control device is preferably designed in such a way as to take into account a further conditional parameter in order to continue the starting, in particular if an interruption takes place or to take into account a general aspect of the laboratory apparatus.

The conditional parameter is preferably influenced by a user input. By waiting for a user input, it is possible to prevent certain operating parameters from being changed automatically. This allows the user particularly to prevent possibly erroneously determined measured values from automatically leading to problematic operating states of the laboratory apparatus. This corresponds to an additional safety enquiry.

The control device is preferably designed for indicating to the user the (items of) information obtained by means of the measured value by means of a user interface device, for example by a display or touchscreen. The control device is preferably designed for evaluating the (items of) information. For this purpose, the control device preferably has the means for evaluation, in particular means for comparison of the measured value.

The control device is also preferably designed for selecting an operating parameter or determining the changing of an operating parameter in dependence of this evaluation. This may take place on the basis of an assignment table, which contains values assigned to one another of the measured value, in particular geometrical properties, of the operating parameter or changes of the operating parameter. The control device is also preferably designed for indicating to the user such a selected operating parameter or selected changing of an operating parameter by means of a user interface device. The control device is preferably designed for receiving a confirmation of the selected operating parameter or the selected changing of an operating parameter by the user by an individual user input or by a number of user inputs taking place by way of a user interface device, and, in dependence on this manual confirmation, continuing or terminating the starting of the process of changing the operating parameter. The control device is preferably designed to allow a user input as a control step. In particular is a user input is allowed as a control step after a comparative operation which either is carried out digitally or analogously. Depending on said user input at least one further control step is carried out. In this way, a semiautomatic handling of the samples is realized, possibly offering the convenience of an automatic preselection, and/or the safeguard of an additional user interaction, to improve further the reliability of the sample handling.

The laboratory apparatus preferably has a user interface device that is signal-connected to the control device, in particular an input device, for example an operator control panel or touchscreen, and/or an output device, for example indicating elements, LEDs, displays, loudspeakers, etc.

The above introduced further conditional parameter, which is preferably taken into consideration during the automatic changing/adapting of the at least one operating parameter or generally during the control step, may also be obtained automatically, for example on the basis of a specific program control. The control device is preferably designed for automatically selecting and establishing an operating parameter in dependence on the measured value, or, depending on the result of a comparison of the measured value, automatically bringing about a changing of the at least one operating parameter as a further control step. This automation is particularly convenient for the user.

The sensor device is preferably arranged in such a way as to interact with the at least one sample vessel element, in order to determine with it at least one measured value that is dependent on the interaction and is representative of the sample vessel element. The fact that the sensor device enters into interaction with the sample vessel device directly during the recording/determination of the measured value means that it is not necessary to provide any additional components of the laboratory apparatus that are coupled to the sample vessel element and bring about an indirect interaction of the sensor device interacting with these additional components. However, this is also possible and provided as an alternative.

The laboratory apparatus preferably has a carrier device for carrying at least one sample vessel element, in which the at least one laboratory sample can be arranged. The at least one sensor device is preferably arranged on said carrier device. This means that the sensor device is preferably arranged within the measuring range of the sensor device in relation to the carrier device.

The at least one sensor device is preferably connected to the carrier device, in particular detachably or preferably undetachably, and preferably integrated in the carrier device, i.e. at least partially enclosed by it. This may have the advantage that the distance between the sensor and the sample vessel element is always constant and the sensor measuring signal can be easily interpreted in the case of an intensity measurement of the response signal.

The carrier device preferably has a receiving region for receiving the at least one sample vessel element. The sensor device is preferably arranged at a distance d from the outer periphery of the receiving region, where d is selected from the preferred ranges that can be formed from the following lower and upper limits (in each case in millimeters): {0; 0.1; 2.0}<=d<={2.0; 3.0; 4.0; 5.0; 8.0; 8.5; 50.0; 100.0; 150.0; 200.0}.

For a specific arrangement of sample vessel element (or the outer periphery of the receiving region) and sensor device, in particular the spatially closest sensor portion, the distance d is measured in such a way that the minimum distance is measured. This may be, for example, the horizontally measured distance between a vertically arranged sensor portion and a vertical outer wall of the sample vessel element. The distance is also preferably measured starting from the sensor portion that emits a measuring beam. This is for example the case with optical sensors (preferably having an optical emitter and detector). The distance is also preferably measured along this measuring beam.

If the sensor device, in particular a sensor portion, is at a distance of 0.0 millimeters from the outer periphery of the receiving region, the sensor portion lies directly against the sample vessel element when the latter is arranged in the receiving region. This has the advantage that a measuring signal measured by the sensor device has a maximum intensity governed by the minimum distance d. The measuring signal is obtained, for example, by emitting a test signal, the reflection of said test signal at the sample vessel element (reflected test signal) and the reception of the reflected test signal (measuring signal) in the sensor device.

Therefore, d should preferably be as small as possible. This also has the advantage that it is unnecessary to use particularly powerful, and consequently relatively voluminous and possibly energy-intensive and costly, sensors. Rather, it is possible to use relatively small sensors with a relatively small mass and volume, whose capacity can be adapted to the small distance d. The proximity of the sensor device to the receiving region, and consequently to the sample vessel elements arranged there, allows the laboratory apparatus to be configured in a space-saving manner in this portion and allows the laboratory apparatus to be compactly designed. Due to such a space-saving arrangement of the sensor it is possible to extend the functionality of the laboratory apparatus without increasing its space requirement. It is also possible and preferred that the sensor device is arranged within the receiving region, preferably at a minimum distance d from the outer periphery of the receiving region.

Preferably, d should be at least 0.1 mm. This makes it easier for the sample vessel element to be inserted into the laboratory apparatus or into the receiving region.

The distance d is preferably at least 2.0 mm. This reduces the risk of the filter to get caught and being scratched when the sample vessel element is inserted into the laboratory apparatus or into the receiving region to a—from a practical viewpoint—tolerable degree.

The distance d is preferably a maximum of 2.0 or 3.0 or 4.0or 5.0 or 5.5 or 6.0 or 8.0 or 8.5 millimeters. In these ranges, the class of sensor devices available on the market on the filing date of this protective right, in particular optical sensors, for example infrared sensors, operate in their optimum range. With d=8.5 mm, the upper limit of the performance class is reached. The next available class of sensor devices is much more expensive because of additional optics and more sophisticated signal processing. Nevertheless, the use of such more sophisticated sensor devices is likewise possible and may produce advantageous arrangement possibilities: in this way, greater distances d are possible, limited only by the typical dimensions of a laboratory apparatus.

A laboratory apparatus is preferably a laboratory apparatus that can be transported by a single user and preferably can be positioned on a typical laboratory worktop (a "benchtop laboratory apparatus"). The laboratory apparatus typically has a relatively compact (projected) standing area, known as the "footprint". The dimensions of the projected standing area, measured at the outermost reaches of the laboratory apparatus in each case, have a width of 150-280 mm and a depth of 170-350 mm. Standard microtitre plates, for example, have a format of 125×85 mm and are usually placed transversely onto the equipment. It is therefore preferably provided that d is at most of such a size that the sensor device can still be positioned horizontally next to a sample vessel element. In particular when the laboratory apparatus is intended also to be able to receive standard microtitre plates, the following preferred values are obtained as maximum distances d: 50.0; 100.0; 150.0; 200.0 millimeters.

The sensor device preferably has means for deflecting or directing a measuring beam, in particular means for deflecting (mirror elements) or directing (light guides, lenses). The sensor device has at least one emitting element for transmitting a measuring beam. The sensor device is preferably arranged such that the emitted measuring beam is deflected by a deflecting means by 90°. The measuring beam may, for example, be emitted vertically upwards and then deflected horizontally. The measuring beam may be reflected horizontally by the sample vessel element and deflected by the same deflecting means vertically downwards again in the direction of the detector. Such an arrangement is space-saving in the horizontal direction, in particular if the sensor device, comprising the sensor emitter and receiver, has a greater spatial extent in the direction of the measuring beam than in at least one direction perpendicular thereto. A purely horizontal arrangement of the sensor device, in particular without the use of a deflecting means, is however likewise possible and preferred. The sensor device is preferably designed as a light barrier, in particular as an infrared light barrier.

The measuring beam (also referred to as the test beam or test signal) may be a light beam in the visible range or in the infrared range. Infrared beams offer the advantage that they can penetrate better regions that would hinder the transmission of visible light, for example a coloured plastic enclosure of the sensor device or impurities on the sensor. Furthermore, infrared beams offer the advantage that they are less common in the spectrum of ambient light than visible wavelength ranges. Thus, when infrared beams are used, the risk of disturbance by the ambient light is reduced. As a consequence, the measurement and the laboratory apparatus are more reliable.

The sensor device is preferably designed for detecting a specific type from a number of predefined types of sample vessel elements and/or adapter elements by using the sensor device, which interacts with a sample vessel element, to generate a measuring signal with which a geometrical property of the sample vessel element can be determined and which is in particular representative of the respective type of sample vessel element measured, so that an unequivocal assignment of the measuring signal to previously known measured values is possible on the basis of the measuring signal (within tolerances), the previously known measured values correlating with the different types of sample vessel elements (see below: assignment table), so that preferably an unambiguous detection is achieved.

The sensor device measures by an interaction with the at least one sample vessel element at least one of the properties thereof and generates a measuring signal, by which a geometrical property of the sample vessel element can be determined. This property is, in particular, the manner and means by which the sample vessel element influences the interaction, for example the changing of the intensity between the incoming test signal and the outgoing changed signal. This interaction may be radiation-based, in particular optical, for example using infrared, visible or invisible radiation; it may also be an electrical interaction, for example measuring a capacitance or impedance, using one or more oscillating circuits; it may also be an ultrasonic interation, preferably contactless, or an mechanical interaction involving contacting. Other sensors are possible, in particular those with which a detection method for detecting a specific type of sample vessel element can also be realized or which offer additional functionality.

The at least one sensor device is preferably designed as a height measuring device for measuring a height of the at least one sample vessel element arranged on the laboratory apparatus. The at least one sensor device has at least one emitting element for transmitting a signal to the at least one sample vessel element and at least one receiving element for receiving a signal modified or reflected by the sample vessel element, the sensor device generating a measuring signal with which the measured value that is representative of the at least one geometrical property of the sample vessel element can be determined.

The height measuring device preferably has a resolution of at least 2 height stages, which means that it can distinguish between at least 2 different heights. This allows the height measuring device to be of a simple embodiment, in particular suitable for distinguishing between two height formats of microtitre plates, that is to say those of "normal" height and deep-well microtitre plates. Preferably the height measuring device has a resolution of 3 or more height stages, in order to be able to distinguish between a greater number of heights.

The sensor device, in particular a light barrier, preferably has at least one emitting element for transmitting a test signal to the at least one sample vessel element and at least one receiving element for receiving a return signal from the at least one sample vessel element, the sensor device generating a (preferably electrical) measuring signal that is representative or characteristic of a property of the sample vessel element. The emitting element may be an LED, preferably an infrared LED, and the receiving element may be a photosensor for receiving such light that is emitted by the emitting element and is reflected by the sample vessel element to be measured. Such LEDs and photosensors are very compact and can be obtained with low mass, so that they are particularly suitable for the present intended use of a compact arrangement. At least one of the two elements, the emitting element and the receiving element, or preferably both elements, is/are preferably arranged on the carrier device, and in particular movable with respect to the laboratory mixing device or the base thereof, so that it/they is/are moved together with the carrier device and the sample vessel element during the mixing movement of said carrier device.

The sensor device is preferably signal-connected to an electronic control device of the laboratory apparatus, so that a measuring signal of the sensor device can be recorded by the control device. The signal link may be wire-bound or wireless. The laboratory apparatus preferably has a data bus system, by way of which the measuring signal is transmitted to the control device, and by way of which the further data can be exchanged, for example also data related to temperature adjustment.

The measuring signal may represent or correspond to a logical value (0/1). The electrical control device and/or the sensor device is then preferably designed for establishing not the signal strength but only the presence (for example "1") or absence (for example "0") of the measuring signal. The measuring signal may, however, also transport the signal strength, that is to say be of a higher resolution. The electrical control device and/or the sensor device is then preferably designed for establishing the signal strength of the measuring signal.

The sensor device may be designed for reading a coding area on the sample vessel element, for example a colour code, grey-scale value, barcode, reflection contrast pattern, etc. This may take place by the evaluation of the signal strength of the measuring signal. A specific sample vessel element or sample vessel element type may be assigned a specific code of the coding area, so that in particular an individual sample vessel element or sample vessel element type can be automatically detected and, in particular, an operating parameter of the laboratory apparatus can be established in dependence on the corresponding measuring signal. The code may contain redundant information, for example contain an error correction, in order to make dependable reading possible.

A coding area, in particular a barcode, may be used particularly for sample tracking, so that information concerning the state of the sample vessel element can be determined and/or logged manually or automatically, preferably by a computer or a laboratory information system (LIS) or LIMS (Laboratory Information Management System). Coding areas on the sample vessel elements could contain, in addition to the type of sample vessel element or as an alternative to that, for example, particulars of the sample contained (identification/name, filling date, volume, batch number). The sample identification may then be stored together with the information concerning the completed preparation program (for example movement parameters such as for example mixing speeds and/or temperatures, in each case with particulars of the duration of the step) in a file in a memory device of the control device, preferably sent by way of a network or subsequently transferred to an external storage medium, for example a USB stick.

In particular if the sensor device is not configured or does not serve as a height measuring device, the sensor device may also be arranged in the receiving region, for example below and/or in contact with the inserted sample vessel element. In this case, the arrangement is even more compact.

Preferably, at least two sensor devices are provided or the sensor device has two components, for example an emitting element and a receiving element. These two sensor devices or components are preferably arranged on opposite sides of the carrier device or of the receiving region and/or are designed in each case for detecting the position of the sample vessel element arranged on the carrier device. In this way it can be dependably detected whether a sample vessel element is arranged correctly on the carrier device. If not, starting of the mixing movement would throw off the sample. This can thus be avoided. The position detection and securement may, however, also be realized with a single sensor device, for example by the presence or absence of a specific measuring signal or a subrange of a measuring signal being evaluated.

The electronic control device is preferably designed for selecting the operating parameter in dependence on the type of the sample vessel element arranged on the carrier element, and preferably designed for detecting this type by means of the measuring signal of the sensor device, by determining the type by way of the at least one measured geometrical property.

The electrical control device preferably has computing means, and in particular programmable circuits, in particular for carrying out one or more control steps. This control step is preferably performed by a computer program. These computing means and/or circuits and/or control steps are preferably designed for performing a program option of a computer program in dependence on the measuring signal that is measured, in particular outputting to the user an indicating signal or an item of information, for example concerning the automatically selected and proposed operating parameter, this indicating signal being dependent on the measuring signal that is measured. The laboratory apparatus is preferably designed so as the user can confirm or set an operating parameter of the laboratory apparatus according to the invention by inputting a user operating parameter by way of a user interface, in order for example to establish at least one movement parameter (for example establishing a mixing movement program, a movement speed and/or movement frequency) or a setpoint temperature value. In this way it is possible in particular to prevent the particular error that, on account of a possibly wrong measurement of the sensor device, an operating parameter is also automatically wrongly set, as would be possible in the case of a fully automatic choice of the operating parameter by the electrical control device. However, this automatic procedure is also possible: it is possible and preferred that the at least one operating parameter is established by the electrical control device automatically in dependence on the measuring signal that is measured.

The electrical control device preferably has data storage means, in particular a memory for an assignment table with values for: the geometrical properties of the at least one sample vessel element;—the types of sample vessel elements, —possible measured values (and preferably tolerances) assigned to these types,—preferably; also operating parameters assigned to these types, preferably a number of different operating parameters of the laboratory mixing device, which is/are intended to be varied in dependence on the type of sample vessel element, in particular movement parameters (for example movement speed or oscillation frequency, amplitude(s)) or setpoint temperature value, for example of a condensation avoidance hood of the laboratory mixing device, or changings of these operating parameters.

The electronic control device, or possibly a number of control devices that are present, may have one or more or all of the following components:—a computing means, for example CPU; microprocessor; data memory device, permanent and volatile data memories, RAM, ROM, firmware, assignment table memory; program memory; program code for controlling the laboratory apparatus, in particular program code for controlling an operating parameter of the laboratory apparatus in dependence on the measuring signal that is measured, program code for controlling the laboratory apparatus according to one or more of the user-established program parameters, for example the kind of mixing movement, sequence of a mixing movement, duration of a mixing movement, temperature-adjusting block setpoint temperature, condensation avoidance hood selection; program code for controlling the energy consumption of the laboratory apparatus (automatic standby); log memory for storing and making available a log file on the control process and/or the operating history of the laboratory mixing device; interfaces for the data exchange, wire-bound or wireless. The laboratory apparatus may also have one or more or all of the following components: a housing, base, framework for carrying the movement device and/or the carrier device; voltage supply, user input device (operator control panel), display, indicator of the detected type of a sample vessel element, (warning) indicator for signalling at least one operating state of the laboratory apparatus; holding device for detachable connection of the exchangeable thermoblock to the carrier device; cover device that can be arranged over the carrier device, in particular condensation avoidance hood.

The carrier device serves for carrying the at least one sample vessel element. The carrier device is designed in particular for carrying the at least one sample vessel element during the handling of the at least one laboratory sample without involving the user of the laboratory apparatus. The carrier device may be of one part or of multiple parts. It may be connected partly or completely undetachably (=not detachable without being destroyed) and/or at least partly detachably (detachable by a user) to the laboratory apparatus, or the base thereof, in particular to a laboratory mixing device or possibly to the movement device thereof or the actuator element thereof, or possibly a coupling portion of the movement device. The carrier device may have a holding device for a sample vessel element. The carrier device may be a peripheral device or have a peripheral device.

The term "peripheral device" refers in the present case to an exchangeable component that can be connected, particularly detachably, to the laboratory apparatus.

The peripheral device is, in particular, an exchangeable block module, i.e. an exchangeable holding device in block form for at least one sample vessel element. The peripheral device can preferably be arranged or fixed on the carrier device or the laboratory apparatus. The laboratory apparatus and/or the carrier device is preferably designed for fastening the peripheral device to the laboratory apparatus and/or the carrier device. The peripheral device may be or have a holding device for a sample vessel element. The peripheral device can also be condensation avoidance hood.

A holding device for a sample vessel element that can be arranged or fixed on the carrier device is preferably provided and preferably consists of plastic, but may also comprise plastic and/or metal, in particular steel, aluminium, silver or one or more of these metals.

The carrier device and/or the peripheral device for a sample vessel element is/are preferably designed for adjusting the temperature of the at least one sample vessel element, by having at least one heat-conducting component or by the carrier device having at least one temperature-adjusting element. They are preferably designed in each case for temperature adjustment, that is to say controlled (or uncontrolled) heating and/or cooling of the samples, in particular using a setpoint temperature as the operating parameter, but having in each case a temperature sensor and/or by being assigned a control loop.

An exchangeable block module preferably comprises at least one material with good thermal conductivity, preferably metal, in particular steel, aluminium, silver or one or more of these materials, or consists of one or more of these materials or comprises plastic or consists substantially of plastic. An exchangeable block module preferably has a frame, which preferably consists of plastic. The exchangeable block module is preferably configured for holding, and preferably thermally contacting, at least one type of sample vessel element, at least by a positive connection. In the case of positive connections, connections for securing the position between components or force transmission are produced by the inter-engagement of partial contours of the connecting elements (see Dubbel, Taschenbuch für den Maschinenbau [Pocketbook for mechanical engineering], 21st edition, 2005, Springer Verlag, chapter G, 1.5.1). An exchangeable block module designed for temperature adjustment is also referred to in the present case as a temperature-adjusting block or thermoblock.

The carrier device or a thermal contacting region of the carrier device preferably has at least one temperature-adjusting device, in particular a Peltier element or a resistive heating element, for example a heating foil, and preferably at least one temperature sensor, which measures the temperature of the temperature-adjusting block at the point of attachment of the temperature sensor by an interaction with the temperature-adjusting block, that is to say a heat flow. The temperature-adjusting device is preferably arranged on the base of the laboratory apparatus. At the same time, or independently thereof, the sensor device is preferably arranged on a peripheral device of the laboratory apparatus. This allows the sensor device to be adapted individually to a specific type of peripheral device, which makes particularly efficient production of the peripheral device and/or efficient use of the sensor device possible, while the functional components for the temperature adjustment or movement of the laboratory apparatus can preferably be used universally for all peripheral devices and arranged in particular on the base of the laboratory apparatus. The measured temperature is used as a measured variable for a control loop, with which the temperature of the temperature-controlled carrier device or of the temperature-adjusting block is controlled. A number of control loops are preferably provided. In a particularly preferred configuration, the temperature-adjusting device is arranged in the carrier device or in the thermal contacting region of the carrier device and the sensor is arranged in the temperature-adjusting block.

The carrier device and a peripheral device that may belong to the carrier device preferably have in each case at least one coupling element which, when the peripheral device is placed onto the carrier device in the defined position, form at least one detachable coupling pair, through which electrical power and/or at least one signal can be transmitted. The respective coupling elements of the at least one detachable coupling pair are preferably galvanically isolated from one another. Electrical power and/or at least one signal can be transmitted through the at least one detachable coupling pair preferably optically and/or inductively and/or capacitively. In this way, an exchange of signals and information can take place between the control device and the peripheral device, in particular whenever the sensor device is arranged on the peripheral device or is connected to it.

The carrier device and/or the peripheral device, in particular the exchangeable block module, preferably has/have an electrical connection system. This may have a number of electrical contacts, for example sprung or unsprung metal contacts, metal connectors, metal sleeves, etc., which can be connected to a number of complementary contacts on the laboratory apparatus, these complementary electrical contacts being established, preferably automatically, in particular when the peripheral device, in particular the exchangeable block module, is placed onto the laboratory apparatus, without any further processes apart from the placement being required. Contactless signal coupling by means of the coupling pairs is also possible. The temperature sensor used for controlling the temperature of the temperature-adjusting block or the temperature-adjusted carrier device is not a component part of the sensor device and must not be confused with it. The electrical controlling device that controls the control is preferably arranged in the laboratory apparatus, preferably in the electrical controlling device of the laboratory apparatus or on the temperature-adjusted carrier device, but may also be arranged on the peripheral device, in particular on the exchangeable block module.

The carrier device or the temperature-adjusting block preferably has an electrical multiple contact system, in the case of which a number of electrical lines are led in the temperature-adjusting block to an electrical multiple contact element lying outside the temperature-adjusting block, which on the side of the laboratory mixing device can be connected to a complementary multiple contact element. The electrical connections of the multiple contact system may lead to various electrical components of the carrier device or of the temperature-adjusting block, for example to the temperature sensor of a temperature-controlling device of the temperature-adjusting block or to one or more sensors of the sensor device or to a controlling device.

A receiving region is preferably provided on the carrier device. The receiving region is preferably configured for receiving one or more sample vessel elements or one or more adapter elements, in particular adapter plates or adapter blocks. An adapter element is preferably configured for receiving at least one sample vessel element. The receiving region preferably has a supporting region, in which the sample vessel element is supported on the carrier device, preferably with at least three support points or support positions, at least one supporting area or supporting frame. The receiving region may have one or more openings, clearances or cavities. The receiving region may be configured so as the sample vessel element can be arranged movably on it, in particular horizontally movable there by means of the excitation movement, for example by plain bearings, rolling contact bearings, etc. on the receiving region.

The carrier device perfectly has a holding device for detachably holding a peripheral device on the carrier device, for example sprung clamping jaws or arresting means, by which the peripheral device is reliably held, in particular with the sample vessel element arranged on it, for example even during a mixing movement. The receiving region is preferably configured for receiving one or more sample vessel elements in a substantially positively engaging manner. In the case of positive connections, connections for securing the position between components or force transmission are produced by the inter-engagement of partial contours of the connecting elements (see Dubbel, Taschenbuch für den Maschinenbau, 21st edition, 2005, Springer Verlag, chapter G, 1.5.1). The receiving region preferably has at least one clearance. The receiving region is preferably provided with a holding device for holding the at least one sample vessel element on this receiving region. A holding device is preferably designed for making possible a connection of the sample vessel element (or of the exchangeable thermoblock or of an adapter element) to the receiving region that can be established and detached again by the user. An exchangeable thermoblock or an adapter element may also have such a holding device.

In a first preferred embodiment of the invention, the laboratory apparatus is designed as a laboratory mixing device for mixing at least one laboratory sample, the at least one operating parameter preferably being a movement parameter that influences the excitation movement, the at least one sensor device preferably being connected to the carrier device, the carrier device preferably being arranged movably on the laboratory apparatus and the laboratory apparatus preferably having a movement device for carrying out an excitation movement of the carrier device, the excitation movement produced by the movement device leading to a movement of the carrier device and of the sensor device connected to the carrier device.

The operating parameter is preferably a movement parameter, in particular a speed variable of the excitation movement, for example a speed of the sample vessel element or of the carrier device along a predetermined movement path, a frequency, for example the frequency of an oscillating movement along an open path or a closed path, for example a circle or ellipse, etc., or an amplitude of this movement. The laboratory mixing device is preferably designed as an orbital mixer, in which the movement takes place substantially parallel to a horizontal plane. This has the advantage that wetting of sample vessel covers can be prevented or reduced.

The movement parameter may also be a changing of these already mentioned movement parameters. It is also possible for a number of these movement parameters to be influenced. If this movement parameter is selected automatically in dependence particularly on the type of sample vessel element, it can be prevented that specific types of sample vessel element, for example deep-well plates, are moved in an unsuitable way, for example too quickly and with excessive centrifugal forces. In the case of laboratory mixing devices of the prior art, for example, throwing off of deep-well plates at high speeds designed for "normal" microtitre plates has been observed. Such situations can be avoided in the case of the described preferred configuration of the invention as a laboratory mixing device.

The movement device may have one or more drives, motors and/or actuators for producing an excitation movement. The movement device may drive one (or more) moved element(s), which is/are coupled in terms of movement to the at least one sample vessel element, in particular the carrier device. One or more coupling portion(s) may be arranged between the moved element and the sample vessel element, which are preferably coupled in terms of movement. The movement device is preferably designed for performing a movement of the sample vessel element, in particular also of the carrier device, in a substantially horizontal plane (with respect to the gravitationally caused planar liquid level of a liquid sample); the movement (=excitation movement or mixing movement) is preferably of an oscillating mode, in particular of a mode oscillating in a substantially circular translatory manner in a plane. Such a mixing movement can preferably be described by two (imaginary) points of the receiving adapter performing a circular movement with substantially the same angular position, same angular speed and same radius. The mixing movement can preferably be selected and/or influenced automatically, for example program-controlled, or by a user.

The carrier device is preferably arranged movably on the laboratory apparatus, so that the carrier device is movable with respect to the laboratory mixing device, in particular a base of the laboratory mixing device, so that the excitation movement produced by the movement device leads to a movement of the carrier device and of the sensor device connected to the carrier device. This offers the further advantage that the sensor measurement does not depend on the relative positioning of the carrier device and the sensor device, since this position remains unchanged. The measurement may, for example, also take place during the movement of the sample vessel element, for example in order to detect the position thereof. The sensor device is preferably arranged exclusively on the carrier device.

The carrier device preferably has a pedestal or frame portion, which preferably partially or completely surrounds the receiving region of the carrier device. The sensor device is preferably integrated in this pedestal or frame portion or connected to it. The pedestal or frame portion is preferably also designed as a holding portion for laterally holding the at least one sample vessel element. The pedestal or frame portion is preferably designed for positively holding and/or surrounding the at least one sample vessel element. The pedestal or frame portion may have further holding means, for example clamps, clasps, bolts, etc. As a holding portion, it is preferably designed for withstanding the accelerations which, in the case of a laboratory mixing device, act on the sample vessel element during the mixing movement of said element and for securely holding the sample vessel element. This multiple function of the pedestal or frame portion makes a particularly compact type of construction of the laboratory mixing device possible.

In a second preferred embodiment of the invention, the laboratory apparatus is designed as a laboratory temperature-adjusting device for heating and/or cooling, in particular as a laboratory temperature-adjusting device for adjusting the temperature of the at least one sample vessel element, the laboratory apparatus preferably having a heating element or a temperature-adjusting element, and/or preferably having a heatable or temperature-controlled cover device for covering the at least one sample vessel element, in particular a condensation avoidance hood, and the operating parameter being a heating manipulated variable or a setpoint temperature of the heating element, of the temperature-adjusting element and/or of the cover device. The term "temperature adjustment" consequently describes setting the temperature to a setpoint value by the controlled changing (increasing or lowering) of said temperature.

A heatable cover device serves for preventing condensation of the sample vapour within the vessels on the inside of the cover by applying a temperature in the cover region of the sample vessel elements that is higher than the temperature of the samples in the sample vessel elements. The operating parameter is preferably a setpoint temperature of the cover device, in particular a condensation prevention hood. The actual temperature of the cover regions that are heated on account of the temperature-adjusted cover device depends on the type or the height of the sample vessel element arranged under the cover device. The automatic detection of the type of sample vessel element or the height of the sample vessel element makes it possible in particular to prevent an unsuitable setpoint temperature of the cover device being used, for example an excessively high setpoint temperature in the case of high deep-well plates.

A laboratory temperature-adjusting device preferably has, preferably on an upper side of the laboratory temperature-adjusting device, a temperature-controlled carrier device for carrying and adjusting the temperature of at least one sample vessel element. The carrier device preferably has a contacting region, which is designed for the thermal contacting of at least one sample vessel element or an exchangeable thermoblock or adapter block. The sample in the sample vessel element is thus heated or cooled indirectly by an active changing of the temperature of the contacting region of the laboratory temperature-adjusting device.

The heated cover device, in particular condensation avoidance hood, preferably encloses together with the housing of the laboratory apparatus and/or the carrier device or a sample-vessel receiving device arranged there (for example exchangeable thermoblock, adapter block, vessel holder) a space above the carrier device. This space, into which the at least one laboratory vessel with sample protrudes, is preferably both temperature-adjusted and also thermally insulated by this heated cover device (or condensation avoidance hood). The heated cover device itself has at least one heating element, for example a heating foil. This heating element of the cover device is usually controlled by the control device, i.e. the temperature-adjusting laboratory apparatus.

The temperature of the heating element in the hood is preferably set in each case higher than the temperature of the contacting region of the laboratory temperature-adjusting device by a specific effective temperature difference of about 10° C., for example between 8° C. and 12° C. This is handled in this way preferably in the case of setpoint temperatures of the contacting region of over 50° C., 60° C. or 70° C. up to 120° C.

It is regarded as inventive particularly in the area of laboratory temperature-adjusting devices to set the temperature of the heating element in the cover device dependent on the measured value, that is to say dependent on the detected sample vessel element, in particular dependent on the detected type of sample vessel element. The device according to the invention consequently has the advantage that even high sample vessel elements, in particular high sample plates, such as for example deep-well plates, do not overheat, melt or catch fire, since such error situations can be avoided by checking the sample vessel element inserted.

The operating parameter may also concern other parameters, which control some function of the laboratory apparatus or of the devices associated with the laboratory apparatus (for example the transporting system for sample vessel elements, manipulating devices, pipetting devices, for example in a robot system, etc.).

In a third preferred embodiment of the invention, the laboratory apparatus is designed as a combined laboratory mixing device and laboratory temperature-adjusting device, which may also have further functions. The invention is not restricted to the laboratory apparatus according to the three preferred embodiments.

The method according to the invention for handling, in particular mixing and/or adjusting the temperature of, at least one laboratory sample arranged in at least one sample vessel element by means of a laboratory apparatus, in particular the laboratory apparatus according to the invention, where the handling of the at least one laboratory sample can be controlled by at least one operating parameter of the laboratory apparatus, comprises the following steps:

measuring at least one measured value that is representative of the at least one sample vessel element and represents in particular the type of the at least one sample vessel element;

controlling the handling of the at least one laboratory sample in dependence on the at least one measured value and on the at least one operating parameter by at least one control step;

preferably: at a time after the obtainment of a starting signal for starting the handling:—preferably starting the at least one control step by which the at least one operating parameter is changed or is not changed in dependence on the at least one measured value recorded; and: —preferably carrying out or not carrying out, in particular terminating or interrupting, the handling according to the at least one operating parameter by this at least one control step, in particular in dependence on the at least one measured value recorded.

In a preferred embodiment of the method and the laboratory apparatus according to the invention, respectively, the method comprises the step of performing a calibration measurement for automatically determining a reference value, and/or the laboratory apparatus is configured for performing a calibration measurement. A calibration measurement improves the reliability of the method and the laboratory apparatus according to the invention.

In case of the implementation of the calibration measurement, the sensor device is preferably configured to be a reflex light barrier. However, the calibration measurement can be provided also with other embodiments. The reflex light barrier has an emitting device for emitting light, preferably a light emitting diode (LED) and a receiving element—preferably a photodiode—for receiving the light, which was emitted and then reflected by a reflecting element, which here is the sample vessel element, preferably a microtiter plate. Upstream to the receiving element, in the pathway of the incoming light, there is preferably a tilted mirror mounted for redirecting the light toward the receiving element, and/or another optical element, like a lens or a filter. A filter is particularly preferred to be arranged in the optical pathway upstream to the receiving element to transmit the wavelength spectrum of the emitting light and preferably substantially block the light with other wavelengths, which are not contained in the emission spectrum of the emitting device. The overall detected light intensity $I_{total}$ of the sensor device, in particular from the receiving device, which receives the light, here a photodiode, is formed by the sum of at least the three components of light intensities, which is the intensity $I_{sig}$ of the signal light I, the intensity $I_{stray}$ of the strayed light, which arrives at the receiving device, in particular light strayed by the optical filter(s) in the pathway, or from other points in the optical pathway, and the intensity $I_{back}$ of the background light, which arrives at the receiving device from the environment, according to:

$$I_{total}=I_{sig}+I_{stray}+I_{back}$$

Said components depend on the light intensity $I_{LED}(\lambda)$ of the emitting element of the sensor device and from the intensity $I_{ambient}$ $(\lambda)$ of the ambient light:

$$I_{sig}=R*F^2(\lambda)*I_{LED} \quad (2)$$

$$I_{stray}=S*I_{LED}(\lambda)$$

$$I_{back}=F(\lambda)*I_{ambient}(\lambda)$$

Hereby, $F(\lambda)$ is the spectrum of the tilted mirror, acting also as an optical filter, S is the stray light factor of the tilted mirror, and R is the reflection factor of the sample vessel element to be detected, here a microtiter plate.

It is the goal of the calibration measurement, to extract the signal fraction from the overall detected light intensity, by separating $I_{sig}$ from the other fractions of light intensities contained in $I_{total}$. Knowing the quantity of $I_{sig}$ allows to draw conclusions about the reflection factor R and thereby about the presence or non-presence, or preferably the height of the sample vessel element.

This can be achieved, in particular, as follows:

1. The stray light $I_{stray}$ is determined, for example, during the startup phase of the laboratory apparatus, for example, directly after powering up the device. For determining the stray light without the ambient light, the sample vessel element is screened light-tight from the environmental light, e.g. be placing a cover element on the sample vessel element or otherwise switching off the environmental light. It is assumed here, that the reflection factor R=0, in case that no sample vessel element is placed in the laboratory apparatus. Then, the stray light intensity is determined to be the difference of the total intensity $I_{total}$ for the LED-light switched on and then switched off:

$$\text{LED off: } I_{total}=0$$

$$\text{LED on: } I_{total}=SI_{LED}(\lambda)$$

$$REF1=\Delta I_{total}=SI_{LED}(\lambda)$$

2. For determining a second calibration measurement during the startup phase, the total intensity $I_{total}$ is measured with the sample vessel element placed in the apparatus and then, without the sample vessel element, while the ambient light is screened, e.g. by placing a cover on the sample vessel element, respectively:

without sample vessel element:

$$I_{total}=S\,I_{LED}(\lambda)$$

with sample vessel element:

$$I_{total}=R*F^2(\lambda)*I_{LED}(\lambda)+S\,I_{LED}(\lambda)$$

$$REF2=\Delta I_{total}=R*F^2(\lambda)*I_{LED}(\lambda)$$

3. Using the two reference values REF1 and REF2, a value for a threshold intensity $I_{thresh}$ is determined as follows ("*" means multiplication):

$$I_{thresh}=REF1+0.5*REF2$$

The value for a threshold intensity is saved in the memory of the laboratory apparatus. The threshold value serves as a reference value for comparing at least one measured value with at least one reference value. Preferably, the calibration measurement is performed at least once for each individual laboratory apparatus, thereby determining $I_{thresh}$ at least once. Is it also possible to remind, e.g. automatically, the user at least once to repeat the calibration measurement, e.g. in a returning manner. It is also possible to determine a default value of $I_{thresh}$, for example by averaging over the results for $I_{thresh}$ from different calibration measurements, e.g. received from several different individual laboratory apparatus, and to save the default value in the permanent memory of the laboratory apparatus, before delivering the laboratory apparatus from the manufacturer to the customer.

4. Once the height determination is activated during operation of the laboratory apparatus, two measurements will be performed: one measurement of the overall signal with the LED being switched off (LED off: $I_{total}$), and one measurement of the overall signal with the LED being switched on (LED on: $I_{total}$):

LED off: $I_{total}=F(\lambda)I_{ambient}(\lambda)$

LED on: $I_{total}=RF^2(\lambda)I_{LED}(\lambda)+SI_{LED}(\lambda)+F(\lambda)I_{ambient}(\lambda)$ Preferably, the two measurements are performed one following directly after the other one, preferably within a time period of 10, 5, 1 or 0.5 seconds. This way, the influence of the ambient light, which may slightly vary over time, can be minimized. It is also preferred that a third measurement is performed, with the LED being switched off, in order to verify, that the difference of the two measurements of the ambient light did not exceed a tolerated quantity for said difference, which quantity preferably was determined before and saved in a memory of the laboratory apparatus.

5. Now the difference of the two total intensities can be determined, preferably, which receives a signal value, which is independent from the ambient light:

$$\Delta I_{total}=RF^2(\lambda)I_{LED}(\lambda)+SI_{LED}(\lambda)$$

Said signal value $\Delta I_{total}$ now is compared with the threshold intensity $I_{thresh}$: the following conditions are defined:

$\Delta I_{total}>I_{thresh}$=>sample vessel element has a first geometric property, e.g. the microtiterplate is from type "DWP"

$\Delta I_{total}<I_{thresh}$=>sample vessel element has a second geometric property, e.g. the microtiterplate is from type "MTP"

Further configurations of the method can be taken from the description of the laboratory apparatus according to the invention and the exemplary embodiments.

The invention also relates to sample vessel elements, in particular disposable sample vessel elements of plastic, in particular multiple vessel plates such as microtitre plates or PCR plates, in particular with an interacting region, in particular a reflection region and/or coding region, which is configured for interaction with the sensor device of the laboratory mixing device according to the invention. A reflection region can specifically change a signal incident there, that is to say provide it with information, and pass it on to a receiving element, that is to say reflect it. This is also possible analogously with a transmission region on the sample vessel element. The interacting region, in particular coding region, allows a reliable automatic detection of the sample vessel element (or type) by the laboratory mixing device according to the invention. The interacting region may be formed integrally with the sample vessel element, in particular by injection-moulding the entire plastic sample vessel element with the interacting region. It may, for example, be designed as a region that can be printed on by machine or manually. Furthermore, the interacting region may be separate from the sample vessel element and connected to the sample vessel element, for example as a sticker, which is for example attached in a marked region of the sample vessel element, for example by the user, and/or is printed on by machine.

Further advantages and features of the invention emerge from the following description of the exemplary embodiment and the figures. In this, the same reference numerals relate substantially to the same components.

FIG. 1 schematically shows an exemplary embodiment of the laboratory apparatus according to the invention.

FIG. 2 schematically shows another exemplary embodiment of the laboratory apparatus according to the invention.

FIGS. 3*a*, 3*b*, 3*c* and 3*d* schematically show in each case another exemplary embodiment of a carrier device of the laboratory apparatus according to the invention with an inserted microtitre plate.

FIG. 4*a* schematically shows an exemplary embodiment of a carrier device with a sensor device of the laboratory apparatus according to the invention, with a low microtitre plate.

FIG. 4*b* schematically shows a diagram with the measuring signals of the sensor device from FIG. 4*a*.

FIG. 5*a* shows the carrier device with the sensor device of FIG. 4*a* with a high microtitre plate.

FIG. 5*b* schematically shows a diagram with the measuring signals of the sensor device from FIG. 5*a*.

FIG. 6*a* schematically shows an exemplary embodiment of a carrier device with another sensor device of the laboratory apparatus according to the invention, with a low microtitre plate.

FIG. 6*b* schematically shows a diagram with the measuring signal of the sensor device from FIG. 6*a*.

FIG. 7*a* shows the carrier device with the sensor device of FIG. 6*a* with a high microtitre plate.

FIG. 7*b* schematically shows a diagram with the measuring signal of the sensor device from FIG. 7*a*.

FIG. 8*a* perspectively shows a further exemplary embodiment of the laboratory apparatus according to the invention, which is used with the exchangeable thermoblock with a sensor device that is shown in FIG. 9*a*.

FIG. 8*b* shows the laboratory apparatus shown in FIG. 8*a* without the exchangeable thermoblock with a sensor device that is shown in FIG. 9*a*.

FIG. 8*c* shows the laboratory apparatus shown in FIG. 8*a* without the exchangeable thermoblock with a sensor device that is shown in FIG. 9*a*, but with the adapter element with a sample vessel holding device that is shown in FIG. 9*d*.

FIG. 9*a* shows the exchangeable thermoblock with a sensor device of the laboratory apparatus of FIG. 8*a*.

FIG. 9*b* shows the exchangeable thermoblock of FIG. 9*a*, in which the 96-well microtitre plate of a low height shown in FIG. 11*a* is inserted.

FIG. 9*c* shows the exchangeable thermoblock of FIG. 9*a*, in which the 96-well microtitre plate shown in FIG. 11*b* of a greater height (deep well) is inserted.

FIG. 9*d* shows the adapter element with a sample vessel holding device that is shown on the laboratory apparatus of FIG. 8*c*.

FIG. 10*a* shows the exchangeable thermoblock with a sensor device of FIG. 9*a*.

FIG. 10*b* shows a detail of the exchangeable thermoblock of FIG. 10*a*.

FIG. 11*a* shows a low 96-well microtitre plate that can be used with the exchangeable thermoblock shown in FIG. 8*a*.

FIG. 11*b* shows a higher 96-well microtitre deep-well plate, which can be used with the exchangeable thermoblock shown in FIG. 8*a*.

FIG. 12 schematically shows another exemplary embodiment of the laboratory mixing device according to the invention.

FIG. 13 schematically shows a further exemplary embodiment of the laboratory apparatus according to the invention, that is to say a laboratory temperature-adjusting device according to the invention with a heated condensation avoidance hood.

Figure 1:
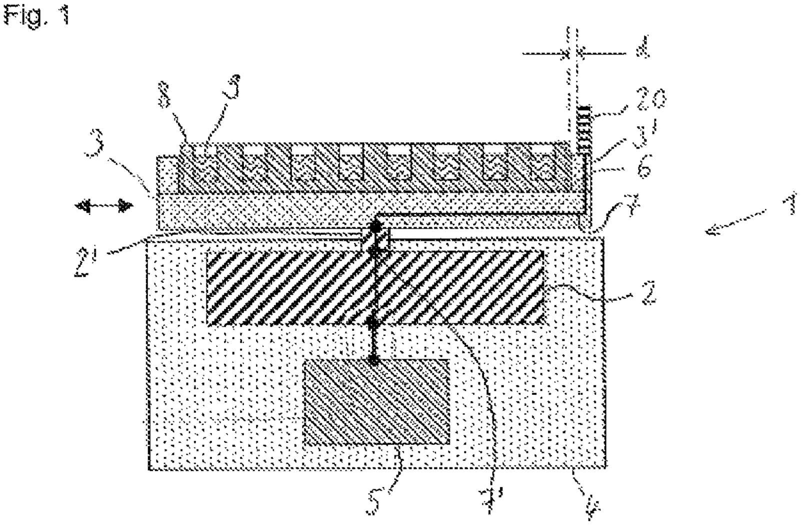

FIG. 1 schematically shows the laboratory mixing device 1 for use in a biochemical laboratory, which is a portable device for a single user, that is to say a benchtop laboratory mixing device 1. The laboratory mixing device 1 has a base 4 with a movement device 2 with a movable coupling part 2'. The laboratory mixing device 1 is designed as an orbital mixer. The movement device is designed such that the carrier device 3 carries out a circular oscillating mixing movement in a horizontal plane for mixing the aqueous samples 9 in the microtitre plate 8, which is arranged in the receiving region 6 of the carrier device and is held by a positive connection. The excitation movement of the movement device 2 is transferred by the horizontally movable coupling part 2' as a mixing movement to the carrier device 3, which is connected fixedly and undetachably to the coupling part 2'. The coupling part 2', the carrier device 3 with the sensor device 20 and the microtitre plate 8 therefore perform the same horizontal movement during the activity of the movement device.

Fixedly connected to the carrier part 3 is the sensor device 20, which is arranged on the frame portion 3', which completely frames the receiving region 6 for the microtitre plate 8 and with which the microtitre plate is captively held on the carrier device during the mixing movement. The sensor device 20 is configured as a height measuring device, which will be explained further with reference to FIGS. 4*a* to 7*b*. For example, it can be detected by the height measuring device whether a lower or a higher standard type of microtitre plate is arranged in the receiving region 6. In dependence on the result of the measurement, the mixing movement is adapted by the control device 5, for example a lower oscillating frequency is applied in the case of a higher microtitre plate than in the case of a lower microtitre plate. The carrier device 3 and the frame portion 3' thereof therefore undertake the dual function of a mounting for the microtitre plate and a measuring device for the height of the microtitre plate. Since the sensor device is arranged on the carrier device, in particular laterally outside the receiving region 6 at a small distance, for example d=0.8 cm, from the periphery of the receiving region, the function of the height measurement can be provided without any further lateral space requirement, since the frame portion 3' is in any case provided as a mounting for the microtitre plate 8.

The sensor device 20 is connected to the control device 5 by way of a cable device 7 with cable connecting points 7', which are shown as black dots. This electrical connection is realized between the movable coupling part 2' and the movement device 2 as a movable cable bundle, one end of which follows the movement of the coupling part.

Figure 2:
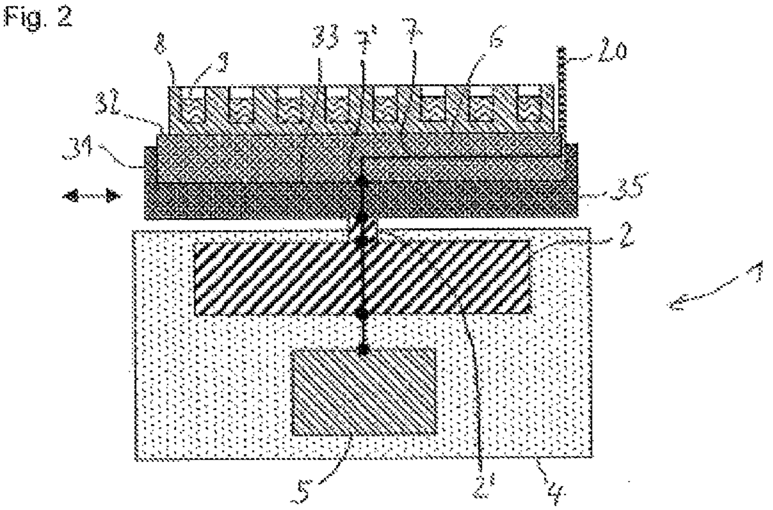

FIG. 2 shows the laboratory mixing device 1, which is constructed in a way corresponding to the laboratory mixing device 1. Instead of a carrier device 3 coupled undetachably to the movement device 2, the laboratory mixing device 1 has a multipart carrier device 30 (that is to say the components 31, 32, 33, 6, 35). The carrier device 30 has a receiving region 33 for receiving the exchangeable thermoblock 32, which is held by the frame portion 31 of the carrier device 30 detachably, but captively during the mixing movement, on the receiving region 33. The mounting of the exchangeable block module 32 on the receiving region 33 may take place by means of frictional connection, for example by use of sprung-mounted clamping jaws (not shown) on the frame portion 31. The exchangeable block module 32 has a receiving region 6 for receiving the microtitre plate 8. The microtitre plate 8 may be held on the exchangeable thermoblock 32 by a positive and/or frictional connection. Laterally with respect to the receiving region 6, the sensor device 20, which is designed as a height measuring device, is arranged on the exchangeable block module 32 and connected undetachably to it. The electrical connection between the sensor device 20 and the electrical control device is designed in the same way as in the case of the laboratory mixing device 1. The electrical contact point 7' between the exchangeable block module 32 and the base part of the carrier device 30 may have a sprung metal contact (not shown), in order to make a dependable electrical connection possible. A magnetic connection between the exchangeable block module 32 and the base part 35 is also possible.

The use of an exchangeable block module 32 with an integrated sensor device has the advantage that it is possible to use different types of exchangeable block module 32, which are suitable for the arrangement of different types of sample vessel elements 8. Since the sensor device is integrated in the exchangeable block module, without changing the horizontal dimensioning of the latter, the carrier device 30, and consequently the laboratory mixing device can be compactly designed, and also without dispensing with the functionality of the sensor device.

Figure 3A:
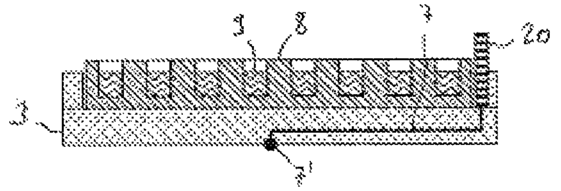

FIG. 3*a* shows the carrier device 3 of the laboratory mixing device 1, with a single sensor device 20.

Figure 3B:
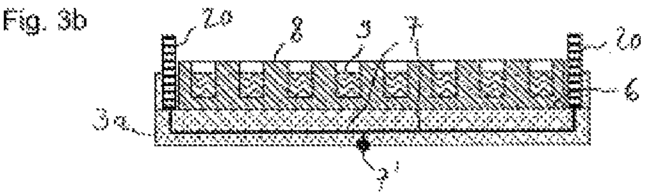

FIG. 3*b* shows the carrier device 3*a*, with two sensor devices 20, which are arranged on opposite sides of the receiving region 6. The use of more than one sensor device allows the positioning of the microtitre plate 8 in the receiving region 6 to be measured even more reliably.

Figure 3C:
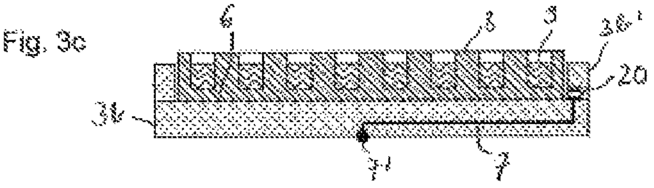

FIG. 3*c* shows the carrier device 3*b* with the sensor device 20, which is designed as an identification device for identifying the type of the sample vessel element 8. Such a sensor device 20 does not have to be arranged along the height of the sample vessel element 8 that is located in the receiving region 6. In FIG. 3*c* it is shown that the sensor device 20 is arranged in the lower region of the inner side of the frame portion 3*b*' or above the height of the bottom of the receiving region 6.

Figure 3D:
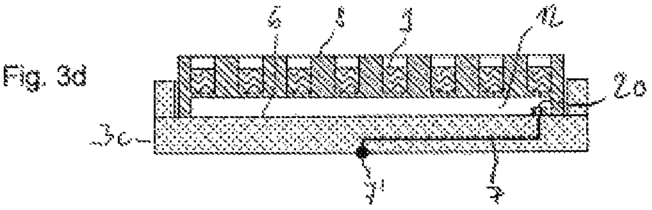

FIG. 3*d* shows the carrier device 3*c* with the sensor device 20, which is also designed as an identification device for identifying the type of the sample vessel element 8. The sensor device 20 is arranged in the receiving region 6 of the carrier device, in particular on the bottom of the receiving region 6. It could, for example, also be arranged in a receiving region 6 of an exchangeable block module 32 (not shown). In this case, the sample vessel element 8 is provided on its underside with a clearance 12 or a cavity 12, into which the sensor device 20 can protrude. Carrier devices or laboratory mixing devices according to the requirements from FIGS. 3*c* and 3*d* can be designed particularly compactly.

An identification device 20 or 20 may also be configured for distinguishing the individual sample vessel element 8 or type of sample vessel element 8 arranged on the carrier device, in particular whether it is a microtitre plate or a PCR plate, etc. The identification device may evaluate a coding region that is arranged on the sample vessel element. For this, the sensor device may have a number of sensors, or have a sensor with a spatial resolution and/or the signal strength of one or more sensors may be evaluated. The coding region may have a contrast region in the manner of a 1D code (for example barcode) or 2D code (for example QR code according to ISO/IEC 18004) or other code. The coding region may also have grey scales or colours, which can for example be evaluated by way of the signal strength.

Figure 4A:
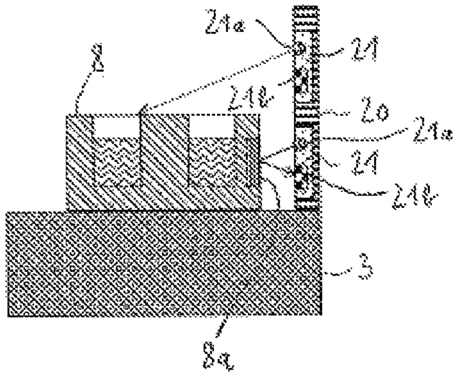

FIG. 4*a* schematically shows an exemplary embodiment of a carrier device 3 with a sensor device 20 of the laboratory mixing device according to the invention, with a lower type of microtitre plate 8. The sensor device 20 is set up as a height measuring device and with a resolution of two different height stages. For this purpose, it has two sensor elements S1, S2 (reference numerals 21, 22), that is to say a lower sensor element S1 and an upper sensor element S2. Each sensor element 21, 22 has a emitting element 21*a* and a receiving element 21*b*. The height measuring device is preferably an optical measuring device. The emitting element is in each case preferably an LED, in particular an infrared LED, and the receiving element is in each case preferably a photodiode.

Figure 4B:
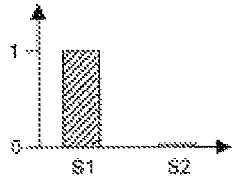

The sample vessel element 8 has a reflection region 8*a*, which reflects the light emitted by the LED 21*a* in the direction of the photodiode 21*b*, which generates an electrical signal, which is made available by the sensor device as a measuring signal to the electrical control device of the laboratory mixing device. In the situation shown in FIG. 4*a*, the sensor element S2 does not measure a signal, since a sample vessel element 8 with a relatively low height h is arranged on the carrier device 3, the sensor element S2 being arranged higher than h. The measuring signal M=(S1, S2)=(1, 0) provided by the two part-signals of the sensor elements 21, 22 is shown in FIG. 4*b*. The value M=(1, 0) of the measuring signal is code for the information that a “normal”, that is to say low, microtitre plate according to the ANSI standard is arranged on the carrier device 3.

Comparing this measured value M with the stored reference value (code) allows the height value of the sample vessel element to be inferred, that is to say whether it is higher or lower than the height of the position of the sensor. The result value of this comparison may be, for example, a logical one if the measured value M=(1, 0) has been determined. The type of sample vessel element is derived from this geometrical property, in particular the presence of a low microtitre plate is determined. Depending on this result value, the control device can in a control step allow and carry out the mixing of the samples according to the operating parameter chosen by the user, for example rotational speed, or automatically set the operating parameter to a suitable value, if required with an interim enquiry to the user, or not carry out the mixing or terminate it if the mixing process is already in progress.

The sensor device is preferably configured such that the reflection region 8*a* of the sample vessel element does not require any particular configuration, since the reflectivity of an outer wall of a conventional microtitre plate is sufficient to reflect the light of the emitting element to the receiving element of the sensor device. However, it is also possible that the reflection region 8*a* of the sample vessel element 8 is configured for reflecting the light, in that it has for example a surface that reflects particularly well, that is to say is relatively smooth.

Figure 5A:
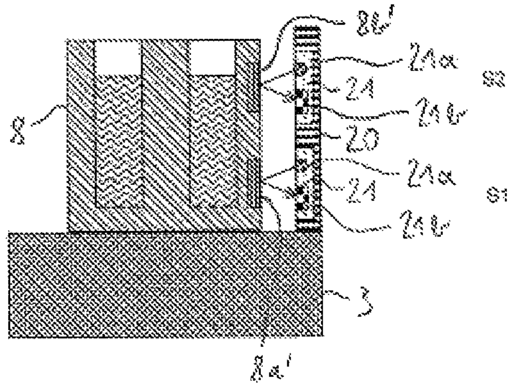
Figure 5B:
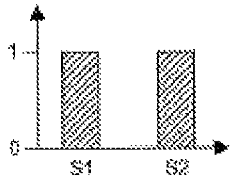

FIG. 5*a* shows the carrier device 3 with the sensor device 20, as in FIG. 4*a*, a high microtitre plate, that is to say a deep-well microtitre plate 8, being arranged here on the carrier device. The sensor device 20 in this case measures a measuring signal M=(1, 1), which is code for the presence of a deep-well microtitre plate.

In the case of the sensor device 20, that is to say height measuring device, which has a measuring resolution of 2 discrete stages, that is to say 2 height stages, 2 sensor elements offer the advantage that a greater measuring certainty is achieved than with a measuring resolution of 1. This is a measurement that determines redundant information that reduces the error susceptibility of the measurement and makes the measurement more reliable. In the case where the measuring signal M produces a value other than (1, 0) or (1, 1), the measurement could be repeated until an admissible value has been determined or the same measured value M has been repeatedly measured and verified. Correspondingly, the mixing movement could be controlled by the electronic control device, and for example the starting of the mixing movement could be prevented in the case of inadmissible measured values M, in particular a warning signal could be output to the user. This applies particularly in the case of the measured value M=(0, 0), that is to say no sample vessel element has been detected. Generally, to implement an error correction, as described, preferably a number N of sensor elements that is greater than the desired measuring resolution A, that is to say N>A, is used, preferably N=M*A, where M is preferably a whole number or real number greater than or equal to 2.

As an alternative to such an error correction, the three measured values M that are possible apart from (0, 0), that is to say (1, 0), (0, 1) and (1, 1), could be used as code for information concerning the measured sample vessel element, that is to say for example to distinguish between three different types of sample vessel elements that are differently configured in each case in such a way that they result in such differing measuring signals. For such a concept, the sensors of a sensor device may also be differently arranged, for example horizontally or in a two-dimensional arrangement.

The information concerning the measured sample vessel element or the type of sample vessel element arranged on the carrier device is preferably used by the electronic control device for adapting an operating parameter of the laboratory mixing device. The adaptation preferably takes place by the electronic control device selecting according to an assignment table stored in a data memory device of the laboratory apparatus which operating parameter is suitable for the measured value that is measured. The selected operating parameter is indicated to the user by way of a user interface device, for example the operator control and indicator panel of FIGS. 8*a*-8*c*. The user then confirms the proposed operating parameter or does not confirm it. Furthermore, the control program (computer program) and the control device are designed such that, after indication of the selected operating parameter or independently of such an indication, that is to say generally, the user inputs its own user operating parameter.

The control program and the control device are then preferably designed for comparing the user operating parameter with the measured value before the starting of the process of changing the operating parameter, and with it establishing the operating parameter (or changing it) and with it commencing the handling of the samples or changing the handling, is brought about by the control program and by the control device. The control program and the control device are preferably designed for comparing the measured value in a digitized form with a comparison value for the presence or absence of a sample vessel element, for example a deep-well plate. In this case, at least one threshold value that defines a tolerance limit may be provided. If the control program and/or the control device establish(es) that, on account of the measured value that is measured, the user operating parameter is not suitable for this measured value, that is to say is not compatible, and for this reason could with a high degree of probability cause an error and damage to the sample, the laboratory apparatus is returned to an initial state (or to an initial value of the operating parameter). This may be the initial state or the initial value may be the state or value before the input of the user operating parameter, or it may be a default state or value. In particular, in such a case an optical and/or acoustic warning signal may be output by the control device.

This operating parameter is preferably a movement parameter of the movement device. A movement speed or movement frequency is preferably selected in dependence on this measured value. In particular, low microtitre plates withstand stronger movement frequencies, and consequently greater accelerations, than higher microtitre plates. In this way it can be prevented that a microtitre plate is operated with an unsuitable movement parameter.

The operating parameter may also be a setpoint temperature for a temperature-adjusted condensation avoidance hood, which is preferably arranged above the carrier device and above the sample vessel elements arranged on it, in order to prevent the condensing of liquid on the inner side of the covers of the sample vessel elements by heating the cover regions of the sample vessel elements above the temperature of the samples contained therein.

Figure 6A:
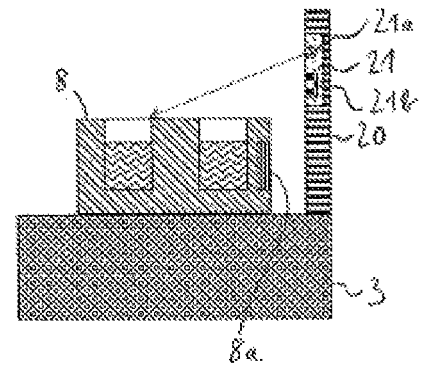
Figure 6B:
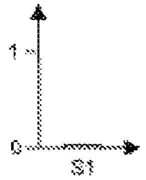
Figure 7A:
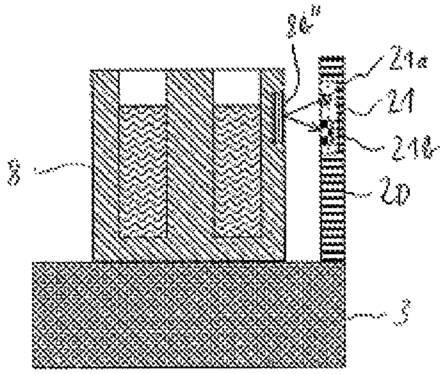
Figure 7B:
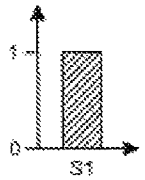

FIG. 6 schematically shows an exemplary embodiment of a carrier device 3 with another sensor device 20 of the laboratory mixing device according to the invention, with a low microtitre plate 8. The sensor device 20 has only a single sensor element 22, which is arranged above the height of the standard microtitre plate 8. In this case, with a single measurement there is no redundant information; the measured value can only be M=0 (FIG. 6*b*) or M=1 (FIG. 7*b*). It is therefore not possible to distinguish whether a low sample vessel element or no sample vessel element is arranged on the carrier device 3. The advantage of the sensor device 20 is, however, that it can be reliably detected relatively simply whether or not a higher sample vessel element 8, for example a deep-well microtitre plate (for example according to the standard), is arranged on the carrier device 3. It can correspondingly be dependably prevented that an unsuitable movement parameter (for example excessive movement speed) is set for a higher sample vessel element 8, or a setpoint temperature value that is unsuitable, because it is too high, is set for a condensation avoidance hood, a value which, in the case of a higher vessel element 8, could overheat and for example damage its cover regions. In the case of the sensor device 20, an error correction can be achieved with only one sensor element, in that the measurement by the electrical control device of the laboratory mixing device is carried out more than just once.

Figure 8A:
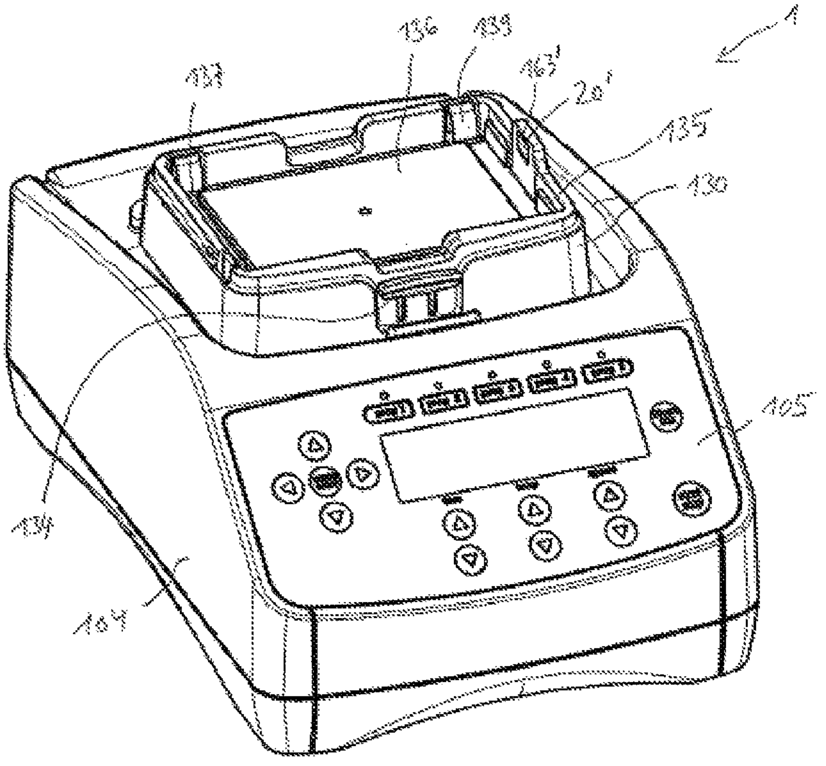
Figure 8B:
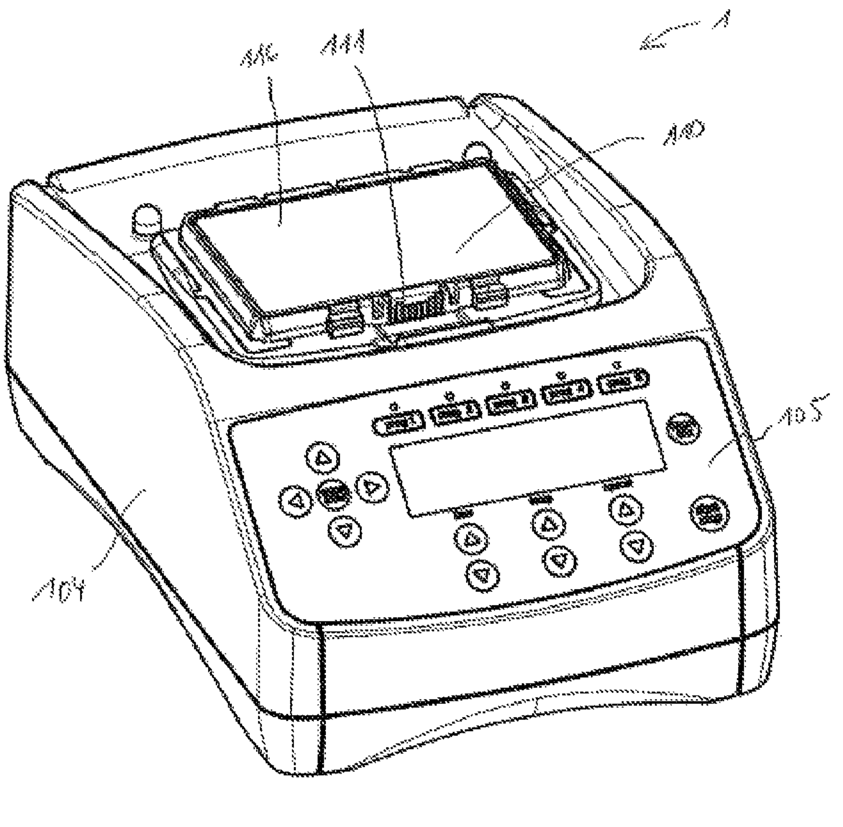
Figure 8C:
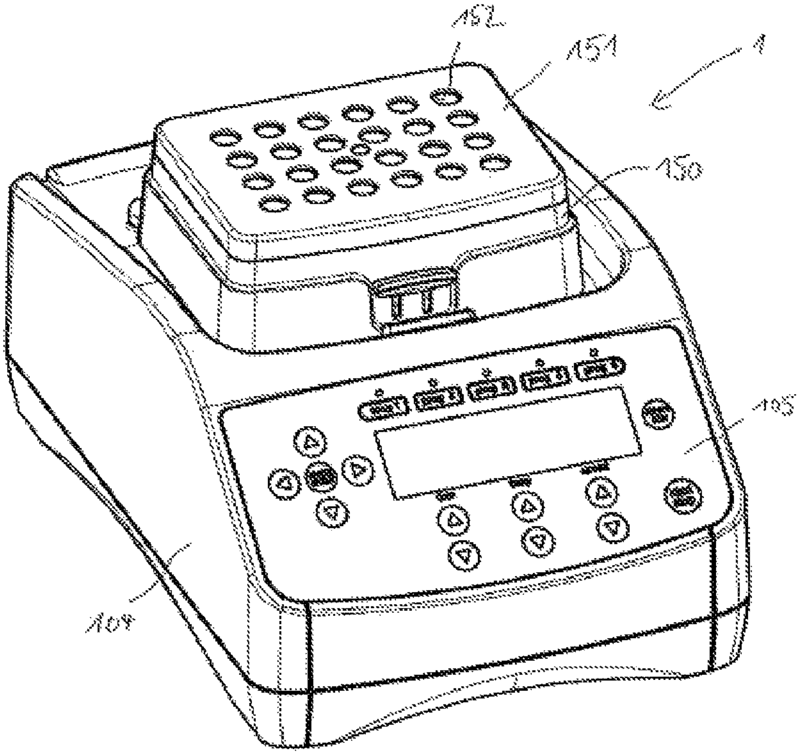
Figure 9A:
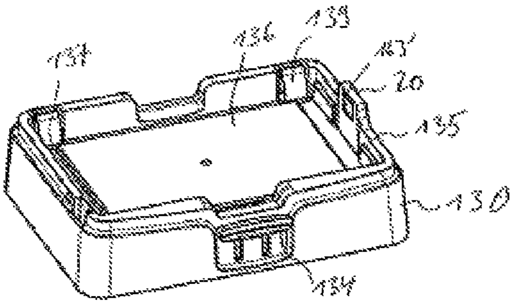
Figure 9B:
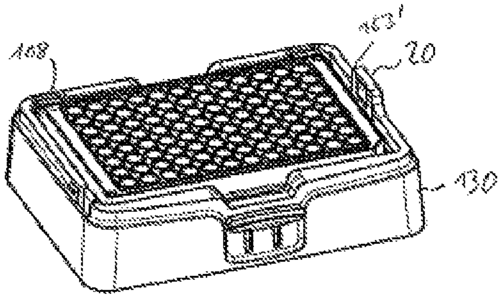
Figure 9C:
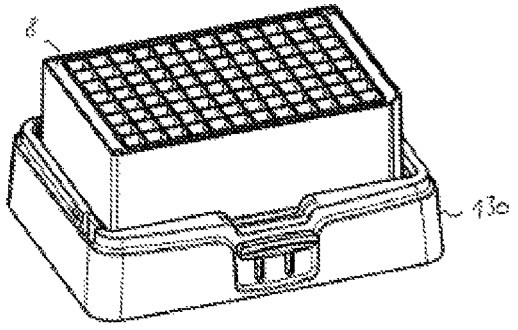

FIG. 8*a* perspectively shows the laboratory apparatus 1 according to the invention, which is used with the exchangeable block module 130 with a sensor device 20 that is shown in FIG. 9*a*. The laboratory apparatus 1 is designed as a combined laboratory mixing device and laboratory temperature-adjusting device, which may for example also be provided with a condensation avoidance hood as a further peripheral device, in a way similar to the laboratory apparatus in FIG. 13. The laboratory apparatus 1 is a benchtop laboratory apparatus. It has a base 104 with a housing 104 with an operator control and indicator panel 105. The dimensions of the laboratory apparatus 1 and the dimensions of the components thereof can be approximately derived from FIGS. 8*a*, 8*b*, 8*c*, 9*a*, 9*b*, 9*c* and 9*d*, if it is taken into consideration that the microtitre plates shown are SBS standard plates. In FIG. 9*c*, the infrared sensor 20 is at a lateral distance of about d=3 mm from the deep-well plate 8, the sensor 20 being covered there by the microtitre plate and not visible. The sensor device 20' has substantially the same functionality as the sensor device in FIGS. 1, 3*a*, 6*a*, 6*b*, 7*a* and 7*b*.

The exchangeable block module 130 is a peripheral device designed as a temperature-adjusting block and has for this purpose a planar contacting region 136 of metal, which is provided in the receiving region between the four walls of the rectangular frame 135. The sensor device 20 is integrated in this frame, to be specific in one of the two shorter side walls of the frame 135. The contacting region 136 is designed as a plate. The plate projects from the upper side 137 of an inner bottom portion of the exchangeable block module 130. This plate engages in a clearance in the bottom portion of a microtitre plate, for example the microtitre plates 8 shown in FIGS. 11*a* and 11*b*. The vessels ("wells") 109, 109' of the microtitre plates are of a planar design on their underside and contact the plate 136 physically and thermally when the microtitre plate is arranged in the receiving region of the exchangeable thermoblock, which is shown in FIGS. 9*b* and 9*c*. The two clamping jaws 139 act as a holding device for the microtitre plates. Using the holding device that can be detached by means of a slide element 134, the exchangeable block module 130 can be arrested on the laboratory apparatus 1, that is to say at a coupling device 110 (FIG. 8*b*). The electrical interface 111 for the electrical contacting of the sensor device has here bent-spring contacts, which are contacted when an exchangeable block module with a sensor device is fixed on the base 104 over the thermal contacting plate 116 by means of the coupling device 110.

The coupling device 110 particularly comprises the thermal contacting plate 116, which is in thermal contact with the contacting region 136 of the exchangeable block module when the latter is connected to the coupling device 110. Arranged below this contacting plate is at least one Peltier element and arranged on the temperature-adjustable exchangeable block module is at least one temperature sensor, this Peltier element and this temperature sensor being assigned to the control loop of an electrical control device of the laboratory apparatus 1. The coupling device 110 also serves for the transfer of a circular, horizontally oscillating excitation movement, which is produced by the laboratory apparatus and is transferred to the coupling device 110 by way of a coupling element (not shown).

FIG. 8*c* shows the laboratory apparatus 1 shown in FIG. 8*a*, without the exchangeable block module with a sensor device that is shown in FIG. 9*a*, but with the adapter element 150 with a sample vessel holding device 151 that is shown in FIG.

Figure 9D:
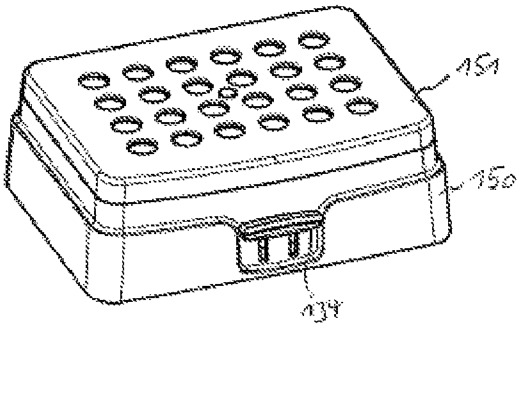

9*d*. FIG. 9*d* shows the adapter element with a sample vessel holding device, which is shown on the laboratory apparatus of FIG. 8*c*. The adapter element 150 is a temperature-adjusting block, similar to the temperature-adjusting block 130. The sample vessel holding device 151 has 24 openings 152, into which in each case an Eppendorf sample tube, here with a capacity of for example 1.5 ml, can be inserted. The sample tubes are in thermal contact with the temperature-adjusting block 150, in order to be adjusted in their temperature, and are also clamped in the opening 152, whereby they are fixedly held on the sample vessel holding device even during a mixing movement.

Figure 10A:
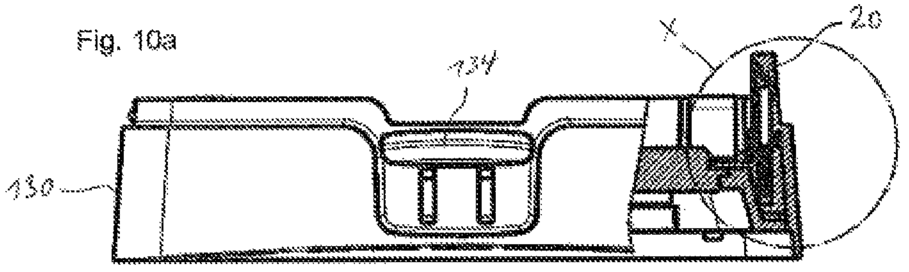
Figure 10B:
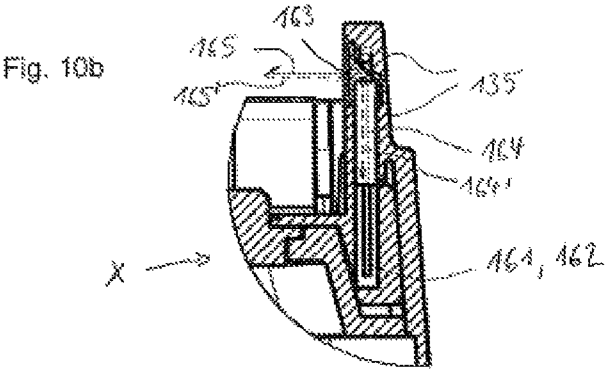

FIG. 10*a* shows the exchangeable block module 130 in side view, and in the region of the sensor device 20 as a cross-sectional view. The detail X of the cross-sectional view is shown enlarged in FIG. 10*b*. Here, the sensor device is fitted into the plastic side wall 135 and substantially enclosed by it. Here, the sensor device 20 has means for deflecting an infrared beam, that is to say a mirror element, which is inclined at an angle of 45° in relation to the horizontal and vertical. The vertical part of the infrared beam emitted by the emitting element 161 is thus deflected into a horizontal beam part 165, and the horizontal beam part 165' that is possibly reflected by a deep-well microtitre plate is deflected into a reflected, vertical beam part 164', which is detected by the receiving element 162 of the sensor device 20. The horizontal beam components pass out of the sensor device 20 and into it through a coloured plastic wall 163'. This plastic "window" 163' is transparent to infrared rays. This type of construction allows the sensor 161, 162, which is several times larger in the vertical direction than in the horizontal direction, to be arranged in a space-saving and efficient manner in close proximity to the receiving region of the exchangeable block module 130 and the sample vessel element.

Figure 12:
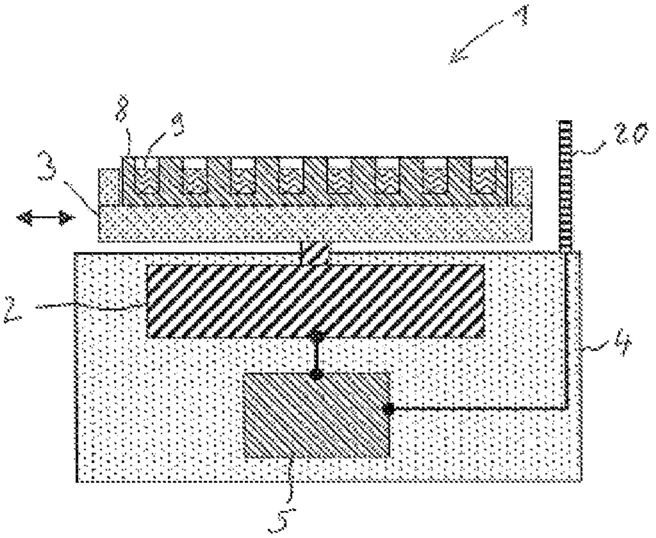

FIG. 12 shows the laboratory mixing device 1. Here, the sensor device 20, designed as a height measuring device, is not arranged on the movable carrier device 3, but immovably on the base 4 of the laboratory mixing device 1, and has substantially the same functionality as the sensor device 20 in FIGS. 1, 3*a*, 6*a*, 6*b*, 7*a* and 7*b*. The control device 5 controls the movement device 2, whereby the carrier device 3 with the sample vessel element 8 can carry out a mixing movement. The sensor device 20 is signal-connected to the control device 5, in order to detect the measured value and, dependent on this measured value, perform the further control steps.

Figure 11A:
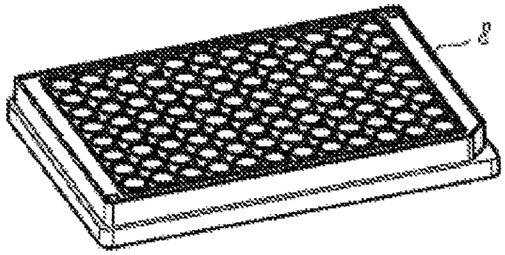
Figure 11B:
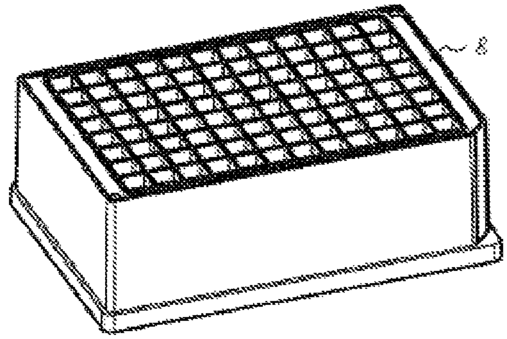
Figure 13:
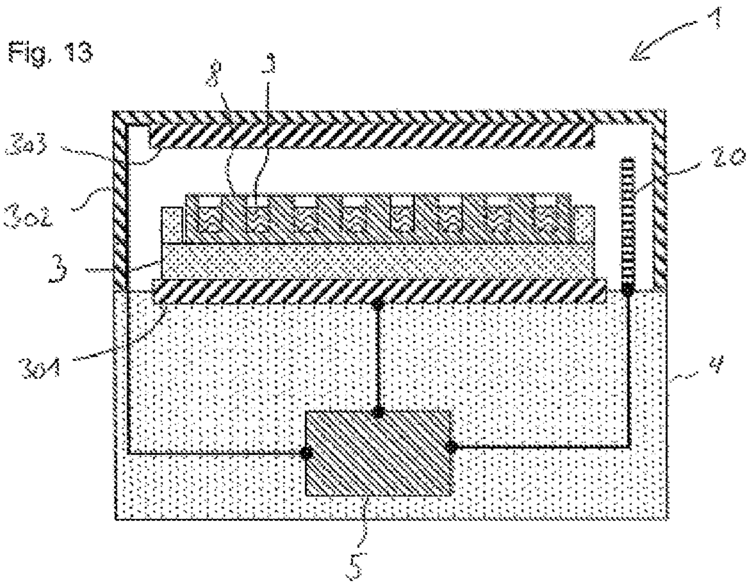

FIG. 13 shows the laboratory temperature-adjusting device 1 with heated condensation avoidance hood 302. The control device 5 is signal-connected to the temperature-adjusting device 301, the cover heating 303 and the sensor device 20, designed as a height measuring device. The control device 5 can detect the measured value by means of the sensor device 20 and, depending on this measured value, perform the further control steps. The sensor device has substantially the same functionality as the sensor device 20 in FIGS. 1, 3*a*, 6*a*, 6*b*, 7*a* and 7*b*. The cover heating 303 is a resistive heating foil. By the checking according to the invention of the sample vessel element 8 arranged on the laboratory temperature-adjusting device 1, it is automatically detected by the control device before the starting of the heating of the heating foil 303 of the cover device 302 that a standard microtitre plate of a low overall height, as shown in FIG. 11*a*, has been inserted. The heating value of the temperature of the heating foil, which in the present case is the operating parameter for the condensation-avoiding handling of the sample vessel element 8, is set higher on the basis of the measured value than would otherwise be the case if a standard microtitre plate of a higher overall height, as shown in FIG. 11*b*, were found. The selection and setting of the operating parameter in this case take place automatically, without user interaction being required. In this way, convenient and reliable operation of the laboratory temperature-adjusting device 1 is achieved.

In a preferred embodiment, the sensor device is configured to be a reflex light barrier, as already described with reference to the embodiments in FIGS. 1, 2*a*, 4*a*, 5*a*, 6*a*, 7*a* and 8*a* to 13. The reflex light barrier has an emitting device for emitting light, here a light emitting diode (LED) and a receiving element—here a photodiode—for receiving the light, which was emitted and then reflected by a reflecting element, which here is the sample vessel element, here a microtiter plate. A calibration measurement is part of the method according to the invention, in the preferred embodiment, and/or is implemented into the laboratory apparatus according to the invention. Reference is made to the description above, which describes the preferred aspects of performing a calibration measurement.

Figure 14:
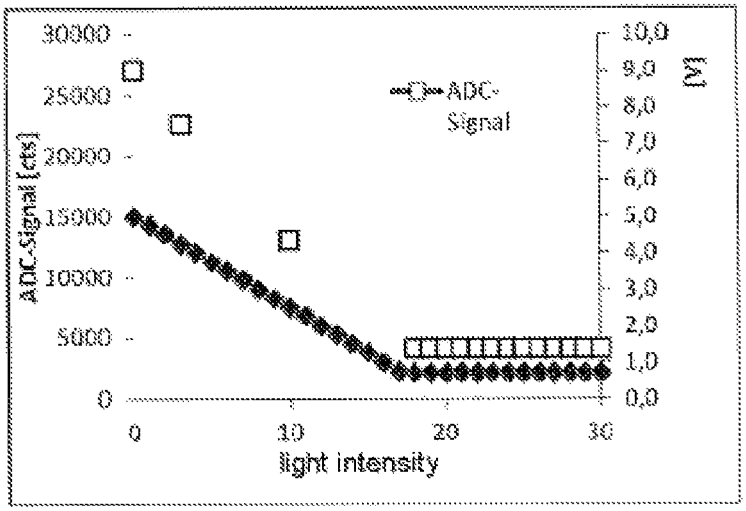
FIG. 14 shows a diagram related to a calibration measurement, according to a preferred embodiment of the method according to the invention and according to a preferred embodiment of the apparatus according to the invention.
Figure 15:
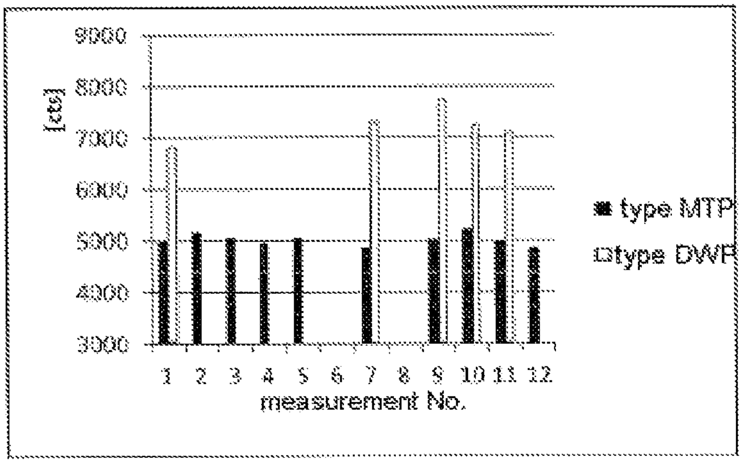
FIG. 15 shows a diagram related to the calibration measurement in FIG. 14.

In the following, the algorithm of the calibration measurement, in a preferred embodiment, is described with reference to the specific embodiment of the laboratory apparatus according to the invention, and with reference to the diagrams in FIGS. 14 and 15. Dark spots indicate the presence of a sample vessel plate of the type "MTP", light spots indicate the presence of a sample vessel plate of the type "DWP" arranged in the reflex light barrier, which has a larger typical height than the MTP-plate. The photodiode of the sensor device puts out a transistor voltage (FIG. 14: "[V]") and a preferably provided analog-to-digital converter ("ADC") puts out digital counts (FIG. 14: "cts"). The correlation between the measured light intensity, the counts (ADC-output) and the transistor voltage is shown in FIG. 14.

In the embodiment shown, the following relationship applies, due to the technical implementation of the measurement: the smaller the light intensity, the higher the transistor voltage and the ADC-output. However, as an alternative, it would also be possible and preferred to implement the measurement according to the alternative relationship: the higher the light intensity, the higher the transistor voltage and the ADC-output. In the present embodiment, the ADC-output varies between a first value, here between 27024 cts, in the case that no light enters the photodiode, and a second value, here 4096 cts, which is the signal saturation value of the photodiode. Signal saturation is achieved, for example, when the apparatus is exposed to the direct sun light. Preferably, the apparatus puts out a warning signal in case of signal saturation.

The calibration measurement takes place, as follows:

1. Calibration measurement 1 (without microtiter plate, the sensor device covered by a cover, here a heated cover, called "Thermotop"):

LED off: $I_{total}$=26988

LED on: $I_{total}$=22456

$REF1$=(26988−22456) cts=4532 cts

2. Calibration measurement 2 (LED on, under Thermotop):

Without microtiter plate: $I_{total}$=22456 (see above)

With microtiter plate: $I_{total}$=20040

$REF2$=(22456−20040) cts=2416 cts

3. Calculation of the threshold value:

$$I_{thresh} = REF1 + 0.5 * REF2 = 5740 \text{ cts}$$

4. Recording of the measured values during the operation of the apparatus and determination of the difference signal. Alternatively, the signal can be recorded twice with the LED being switched off, preferably one measurement before the measurement with LED and one after it, in order to reduce the effects of a varying ambient light.
5. Determination of the difference between the values with the LED being switched on and switched off. Typical values of the value $\Delta I_{total}$ are shown in FIG. 15. Difference values $\Delta I_{total}$ under the threshold of 5740 cts are recognized to indicate the presence of a microtiter plate from type MTP in the reflex light barrier, larger values are identified to refer to a microtiter plate from type DWP.

The invention claimed is:

1. Laboratory apparatus for handling at least one laboratory sample, for mixing and/or adjusting the temperature of a biochemical laboratory sample, which is arranged in at least one sample vessel element, having a carrier device for carrying the at least one sample vessel element, an electrical control device, which is set up for controlling the laboratory apparatus, and at least one sensor device for recording at least one measured value, by which at least one geometrical property selected from the group consisting of a height value, width value, depth value and a logical result value of a geometrical comparison of the at least one sample vessel element can be determined, the measurement using a radiation based interaction with the at least one sample vessel element, the at least one sensor device having at least one emitting element for transmitting a radiation signal to the at least one sample vessel element and at least one receiving element for receiving a radiation signal modified or reflected by the sample vessel element or a light-barrier signal and being signal-connected to the electrical control device, and the electrical control device being set up for controlling the handling of the at least one laboratory sample in dependence on the at least one measured value and the at least one operating parameter by at least one control step, wherein the laboratory apparatus is designed as a laboratory mixing device for mixing at least one laboratory sample, the at least one operating parameter being a movement parameter that influences the excitation movement, the at least one sensor device being connected to the carrier device, the carrier device being arranged movably on the laboratory apparatus and the laboratory apparatus having a movement device for carrying out an excitation movement of the carrier device, the excitation movement produced by the movement device leading to a movement of the carrier device and of the sensor device connected to the carrier device, or wherein the laboratory apparatus is designed as a laboratory temperature-adjusting device for adjusting the temperature of the at least one sample vessel element, having a temperature-controlled cover device for covering the at least one sample vessel element, and the operating parameter being a setpoint temperature of the cover device.

2. Laboratory apparatus according to claim 1, characterized in that the electrical control device is set up for performing the at least one control step after the obtainment of a starting signal for starting the handling according to the at least one operating parameter, the at least one operating parameter being changed or not changed by this at least one control step in dependence on the at least one measured value recorded and the handling being carried out or not carried out by the at least one control step according to at least one operating parameter.

3. Laboratory apparatus according to claim 1, wherein the measured value is a standard type selected from the group consisting of ANSI/SBS 1-2004, ANSI/SBS 2-2004, ANSI/SBS 3-2004 and ANSI/SBS 4-2004, of the at least one sample vessel element, and the control device is set up for carrying out in this at least one control step a comparative operation, in which the measured value is compared with previously known sample vessel type data and the type is detected, and for carrying out the setting of the at least one operating parameter in dependence on the result of this comparison.

4. Laboratory apparatus according to claim 3, characterized in that this measured value represents an individual sample vessel element, and the control device being designed for using this measured value and the comparative operation to distinguish the individual sample vessel element from a multiplicity of other individual sample vessel elements.

5. Laboratory apparatus according to claim 1, characterized in that the control device is set up for measuring in this at least one control step the at least one measured value by means of the sensor device.

6. Laboratory apparatus according to claim 1, which also has a user interface device signal-connected to the control device, the control device being designed for providing a user input in this at least one control step, and for setting the at least one operating parameter dependent on this user input.

7. Laboratory apparatus according to claim 3, characterized in that the control device is designed for automatically bringing about a changing of the at least one operating parameter dependent on the result of this comparative operation.

8. Laboratory apparatus according to claim 1, characterized in that the sensor device is arranged for interaction with the at least one sample vessel element in such a way that at least one measured value that is dependent on this interaction and is representative of the sample vessel element can be determined.

9. Laboratory apparatus according to claim 1, characterized in that the at least one sensor device is arranged on the carrier device.

10. Laboratory apparatus according to claim 1, characterized in that the carrier device has a receiving region for receiving the at least one sample vessel element and in that the sensor device is arranged at a distance d from the outer periphery of the receiving region, where d is selected from ranges that are formed from the following lower and upper limits (in each case in millimeters): {0; 0.1; 2.0}<=d<={2.0; 3.0; 4.0; 5.0; 8.0; 8.5; 50.0; 100.0; 150.0; 200.0}.

11. Laboratory apparatus according to claim 1, characterized in that the at least one sensor device is designed as a height measuring device for measuring a height of the at least one sample vessel element arranged on the laboratory apparatus.

12. Laboratory apparatus according to claim 1, characterized in that the at least one sensor device is designed as a reflex light barrier.

13. Laboratory apparatus according to claim 1, which is designed as a laboratory temperature-adjusting device for adjusting the temperature of the at least one sample vessel element, wherein the temperature-controlled cover device is a condensation avoidance hood.

* * * * *